United States Patent [19]

Charpiot et al.

[11] Patent Number: 4,985,550

[45] Date of Patent: Jan. 15, 1991

[54] POLYHYDROXYLATED AND HIGLY FLUORINATED COMPOUNDS, THEIR PREPARATION AND THEIR USE A S SURFACTANTS

[75] Inventors: Brigitte Charpiot; Jacques Greiner; Maurice Le Blanc; Alexandre Manfredi, all of Nice; Jean Riess, Falicon; Leila Zarif, Nice, all of France

[73] Assignee: Alliance Pharmaceutical Corp., Otisville, N.Y.

[21] Appl. No.: 78,626

[22] Filed: Jul. 28, 1987

[30] Foreign Application Priority Data

Jul. 29, 1986 [FR] France .................... 86 11084

[51] Int. Cl.$^5$ .................... C07H 5/02; A61K 31/70
[52] U.S. Cl. .................... 536/18.4; 536/4.1; 536/18.5; 536/18.6; 536/122; 424/5; 514/832; 514/908
[58] Field of Search .................... 536/18.4, 4.1, 18.5, 536/18.6, 122; 424/5

[56] References Cited

U.S. PATENT DOCUMENTS

| | | | |
|---|---|---|---|
| 2,891,052 | 6/1959 | Boettner et al. | 536/53 |
| 3,839,318 | 10/1974 | Mansfield | 536/18.6 |
| 3,952,066 | 4/1976 | Glickman et al. | 568/615 |
| 4,089,804 | 5/1978 | Falk | 252/355 |

FOREIGN PATENT DOCUMENTS

| | | | |
|---|---|---|---|
| 1468176 | 12/1968 | Fed. Rep. of Germany. | |
| 2144122 | 2/1985 | United Kingdom. | |
| 2181734 | 4/1987 | United Kingdom | 536/18.4 |

OTHER PUBLICATIONS

French Patent Office Search Report, Oct. 23, 1987 FR 8611084.

*Primary Examiner*—Ronald W. Griffin
*Attorney, Agent, or Firm*—Knobbe, Martens, Olson & Bear

[57] ABSTRACT

Compounds having a polyhydroxylated hydrophilic moiety, a highly fluorinated moiety and a functional junction group linking said moieties together, wherein said hydrophilic moiety is derived from a polyol or an aminopolyol, and wherein said highly fluorinated moiety consists of a fluorocarbon group wherein at lest 50% of the atoms bonded to the carbon skeleton are fluorine atoms, the other atoms bonded to the carbon skeleton being hydrogen, chlorine or bromine atoms, said highly fluorinated moiety containing at least 4 fluorine atoms; as well as the internal ethers and ketals thereof; process for their preparation; and a compositions containing said compounds as surfactants, together with non polar compounds, for use as gas carriers.

16 Claims, No Drawings

POLYHYDROXYLATED AND HIGHLY FLUORINATED COMPOUNDS, THEIR PREPARATION AND THEIR USE AS SURFACTANTS

The present invention concerns new chemical compounds which contain a substituent which can be considered as "highly fluorinated", their preparation and their application as surfactants, in particular in compositions intended for biomedical employment as oxygen carriers, administrable intravascularly or through other routes. Such compositions and certain of their applications have been described by M. LE BLANC and J. G. RIESS, in "Preparation, Properties and Industrial Applications of Organofluorine Compounds, Chap. 3, R. E. BANKS Ed., Ellis Horwood Ltd., Chichester, 1982". Among these compositions, one can cite those which are themselves fluorocarbon-based and are usable as blood and plasma substitutes, preparations for the treatment of cerebral and cardiac ischemia or for sensitization of tumors to radiation or chemotherapeutic agents, cardioplegic and reperfusion solutions, diagnostic agents, and non intravascular oxygenating agents, for example for preservation of isolated organs and tissues, or for perfusion of the brain by the ventriculo-sub-arachnoid route.

The applications of these new compounds can be attributed to their surfactant and biocompatibility properties.

Furthermore, they can be used as a co-surfactants, when a small proportion induces a synergistic effect with another surfactant of a different nature, such as lecithins or alkylene oxide block polymers similar to those marketed under the "Pluronic" trademark, in any application where at least one surfactant is required.

For several years, fluorocarbon emulsions have been described, in which synthetic chemical compounds assure, in particular the transport of oxygen to the tissues, and of carbon dioxide to the lungs, and some of which can simultaneously fulfill still other functions, such as those of a diagnostic contrast agent, a vehicle for nutritive and/or medicinal substances or analogues thereof. These compounds belong to the general class of fluorocarbon and perfluoralkylated derivatives, in a broad sense, and, due to their insolubility in plasma or water, they must be maintained in an emulsion by means of one or more surface active agents. Nevertheless, despite the progress made in this field, a certain number of difficulties and drawbacks remain, that have not been resolved, as described by J. G. Riess in "Artificial Organs", Vol. 8 (1), pp. 44-56 (1984), as well as in the periodical "Life Support Systems", vol. 2 (4), pp. 273-276 (1984).

In fact, the properties of the surfactants known and in use to date are still insufficient for the mastery of the emulsions, especially with regard to their intravascular persistence and their stability.

Furthermore, many surfactants are toxic and they are obviously not biomedically acceptable. Thus, even the lecithins, whose use is wedely advocated in this field, are not very stable and can produce toxic decomposition or oxydation products.

The present invention rests on the discovery that a particular family of surfactants and co-surfactants belonging to the new class discussed herein, does not suffer these disadvantages but possesses, on the contrary, properties which are particularly appropriate to the aforementioned applications.

The present invention relates to chemical compounds having a polyhydroxylated hydrophilic moiety, a highly fluorinated moiety and a functional junction group linking said moieties together, wherein said hydrophilic moiety is derived from a polyol or an aminopolyol, and wherein said highly fluorinated moiety consists of a fluorocarbon group wherein at least 50% (and particularly at least 60%) of the atoms bonded to the carbon skeleton are fluorine atoms, the other atoms bonded to the carbon skeleton being hydrogen, chlorine or bromine atoms, said highly fluorinated moiety containing at least 4 (and generally 5) fluorine atoms; as well as the internal ethers and ketals thereof.

The functional junction group is for example one which allows to link the hydrophilic and fluorinated moieties through an ether, ester, amide or amine group.

The hydrophilic moiety is for example derived from a sugar (such as aldopentoses, ketopentoses, aldohexoses, ketohexoses, 6-deoxyaldohexoses, 6-deoxyketohexoses), from a polyol (other than a sugar) containing at least 4 hydroxyl groups (such as pentitols, 1-deoxyhexitols, hexitols, cyclitols), from an aminopolyol having at least 3 hydroxyl groups (such as 1-amino-1-deoxypentitols, osamines, 2-amino-2-deoxypentitols, 1-amino-1,6-dideoxyhexitols, 1-amino-1-deoxyhexitols), or from a diholoside (such as maltose, lactose, saccharose or cellobiose).

The highly fluorinated moiety ($R_F$) may be introduced for example as a $R_F$—W— group, wherein $R_F$ is selected from the group consisting of:

| | |
|---|---|
| $F(CF_2)_v$— | with $2 \leq v \leq 12$ |
| $(CF_3)_2CF(CF_2)_w$— | $0 \leq w \leq 8$ |
| $R_{F1}[CF_2CF(CF_3)]_r$— | $1 \leq r \leq 4$ |

$R_{F1}$ being $CF_3$—, $C_2F_5$— or $(CF_3)_2CF$—,

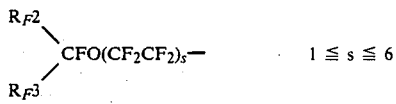

$1 \leq s \leq 6$ $R_F2$ and $R_F3$, identical or different, being selected from $CF_3$—, $C_2F_5$—, n—$C_3F_7$ or $CF_3CF_2CF(CF_3)$—, or $R_F2$ and $R_F3$ representing together —$(CF_2)_4$— or —$(CF_2)_5$—,

| | |
|---|---|
| $CF_3CF_2O(CF_2CF_2O)_tCF_2$— | $0 \leq t \leq 6$ |
| and | |
| $CF_3(CF_2)_2O[CF(CF_3)CF_2O]_uCF(CF_3)$— | $0 \leq u \leq 6$ | and W is selected from the group consisting of:
—$(CH_2)_n$—
—$(CH_2)_pCH=CH—(CH_2)_q$—
—$(CH_2)_m$—CO—
—$(CH_2)_jOCH_2CH(OH)CH_2$— and
—$(CH_2)_kOCH_2CH(CH_2OH)$—
(wherein in the last three cases $R_F$ is bonded to the carbon atom of the left end of the W group),
wherein
n may vary from 1 to 12,
m may vary from 0 to 12,
the sum (p+q) may vary from 1 to 12,
j and k may vary from 1 to 12,
it being understood that W can still contain a —$(CH_2CH_2O)_y$— polyoxyethylene-type, a —(―CH(CH₃)CH₂O―)ᵧ— polyoxypropylene-type or a —(CH₂CH₂S)ᵧ— polythioethylene-type segment, or a mixture of such segments, with $1 \leq y \leq 12$, and that in the $R_F$— chain, part of the fluorine atoms can be replaced by H, Cl or Br atoms, in a proportion such that at least 50% of the atoms bonded to the carbon skeleton of $R_F$— are fluorine atoms, with at least 4 fluorine atoms being present in said chain.

When $R_F$—W— is an acyl group, i.e. when W is —(CH₂)ₘ—CO—, it may be linked with the hydrophilic moiety either by an ester bond (formed with a hydroxyl group of the hydrophilic moiety) or by an amide bond (formed with an amine group of the hydrophilic moiety). In the other cases, $R_F$—W— is linked with the hydrophilic moiety through an ether bond or a —N(R'')— amine bond, wherein R'' may represent —H, C₁-C₁₈ alkyl, C₂-C₁₈ unsaturated alkyl, or R'' may represent a $R_F$—W— group as defined above.

Preferably, the compounds according to the present invention contain 1 or 2 $R_F$—W— groups; also preferably, at least 60% of the atoms linked to the carbon skeleton of $R_F$ are fluorine atoms, and $R_F$ carries at least five fluorine atoms.

The invention particularly relates to the compounds, as defined above, wherein $R_F$ is a perfluorinated group.

The compounds according to the invention comprise those which are derived from the substitution, by a highly fluorinated substituent, of at least one of the hydrogen atoms of the hydroxyl or amino groups carried by a compound of the formula (II)

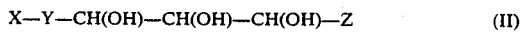

X—Y—CH(OH)—CH(OH)—CH(OH)—Z    (II)

wherein X, Y and Z are as defined hereafter.

Thus, the invention relates particularly to the compounds of the formula I

X—Y—CH(OR₁)—CH(OR₂)CH(OR₃)—Z    (I)

wherein:
X represents —CH=O, —CH₂OR₄, —CH₂N(R₅)R₆ or —CH(OR₇)—,
Y represents —CH(OR₈)—, —CO— or —CH(NR₅R₆)—,
Z represents —H, —CH₃, —CH₂OR₉ or —CH(OR₁₀)—,
it being understood that:
when X is —CH=O, then Y represents —CH(OR₈)— or —CH(NR₅R₆)—,
when X is —CH₂N(R₅)R₆, then Y represents —CH(OR₈)—,
when Z is —CH(OR₁₀)—, then X represents —CH(OR₇)— and then the divalent groups X and Z are linked together through a covalent bond, and when Y is —CH(NR₅R₆)—, the X represents —CH=O or —CH₂OR₄, and the R₁ to R₁₀ groups, which may be identical or different, are selected from —H, C₁-C₁₈ alkyl, C₂-C₁₈ unsaturated alkyl, a deoxy-oside group, a —(CH₂C-H₂O)ᵧ—H, —[CH(CH₃)CH₂O]—H or —(CH₂CH₂-S)ᵧ—H group, or a mixture of said groups, wherein $1 \leq y \leq 12$, and a highly fluorinated group as defined above, with the proviso that at least one of the R₁ through R₁₀ groups represents a group having a highly fluorinated substituent, said group being for example of the $R_F$—W— type as defined above; as well as internal ethers and ketals thereof.

The invention relates particularly to the compounds of formula I wherein the non-fluorinated R groups attached to oxygen atoms of the polyol or amino-polyol represent —H.

Of course, when one of the R substituents is a deoxy-oxide group, the basic hydrophilic moiety is a diholoside, and each sugar moiety of the diholoside may carry a highly fluorinated substituent.

In many cases, the compounds of formula I may comprise open forms, tautomeric or analogous forms, or cyclic derivative structures, as described for example in the "Handbook of Biochemistry and Molecular Biology, Lipids, Carbohydrates, Steroids", 3rd Ed., CRC Press, 1975. The formula I likewise implies no limitation at all with regards to a particular stereochemistry.

For example, when X represents CHO, and Y is CHOH, the compounds of formula I are derived from an aldose type sugar, the structure of which can adopt the tautomeric forms (IA), (IA₁) and (IA₂):

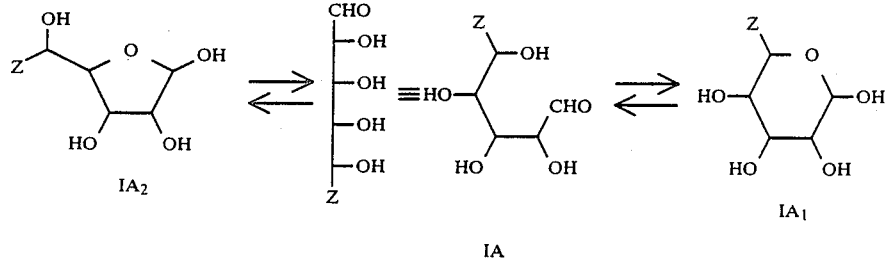

IA₂     IA     IA₁ the structure (IA) representing the open form, while the structures (IA₁) and (IA₂) represent the cyclic (or acetal) forms, i.e. a pyranose (IA₁) and a furanose (IA₂), respectively.

In this first case, if in formula (IA),
Z represents CH₂OH, the formula represents the various hexoses, such as glucose, galactose, mannose, etc.;
Z represents H, the formula represents the various pentoses, such as ribose, arabinose, xylose, etc.;
Z represents CH₃, the formula represents the various deoxy-6-hexoses, such as rhamnose, fucose etc.

Likewise, when, in the formula I, X represents CH₂OH, then two cases are possible:

In the case where Y represents C=O, one obtains a family of cetose type sugars whose basic structures can adopt the open (IB), and the cyclic (IB₁) and (IB₂) tautomeric forms, which in the example where Z equals CH₂OH, are the hexocetoses which have the following structures:

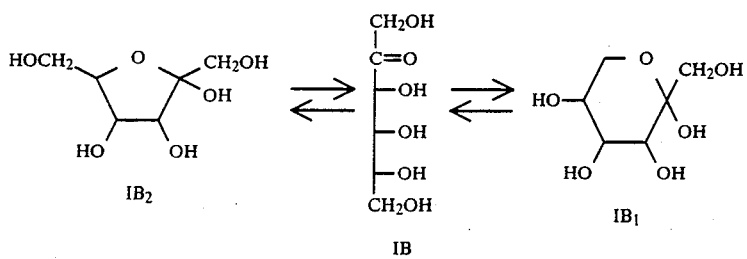

These structures are those of diverse hexocetoses, of which fructose is a typical example, structure (IB$_1$) representing its pyranose form and structure (IB$_2$) representing its furanose form. Other sugars in this family are those resulting from the association of compounds derived from those represented by formulas (IA) and/or (IB), such as, for example, sucrose, lactose, maltose and cellobiose.

in the case where Y represents CHOH, the basic structure represents the family of polyols (IC)

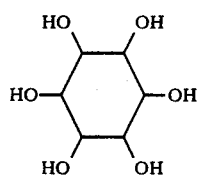

when Z represents CH$_2$OH, the basic structure is that of hexitols such as, for example, mannitol, sorbitol, etc., when Z represents H, the basic structure is that of pentitols such as, for example xylitol, and when XZ represents (CHOH)$_2$, the basic structure is that of cyclitols, of formula (ID):

such as for example inositol.

The aforementioned hexitols (IC), by dehydration, lead to the manoanhydrides (II A), then to the dianhydrides (II B) according to the following diagram:

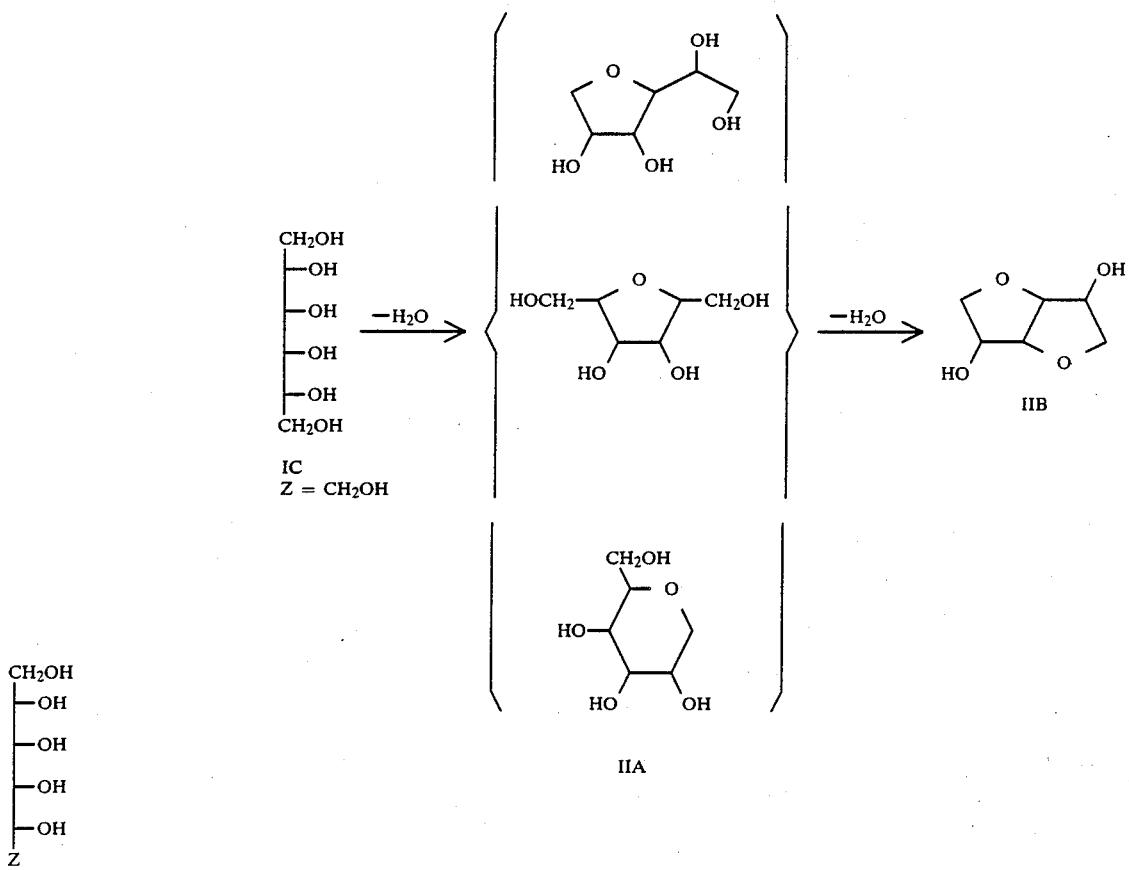

when X represents CH$_2$NH$_2$ or CH$_2$N(R$_5$)R$_6$ and therefore Y represents CHOH, the basic structure represents the aminopolyols, of which glucamineie is a good example, in which Z represents CH$_2$OH

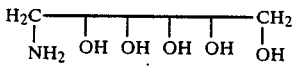

IE

It goes without saying that all of the isomers represented by the preceding various formulas are included in the scope of the present invention.

One should also note that when a substituent R represents another saccharide radical, this radical can derive in particular from glucose, galactose or fructose, and have pyranose of furanose cyclic forms such as, for example, the following:

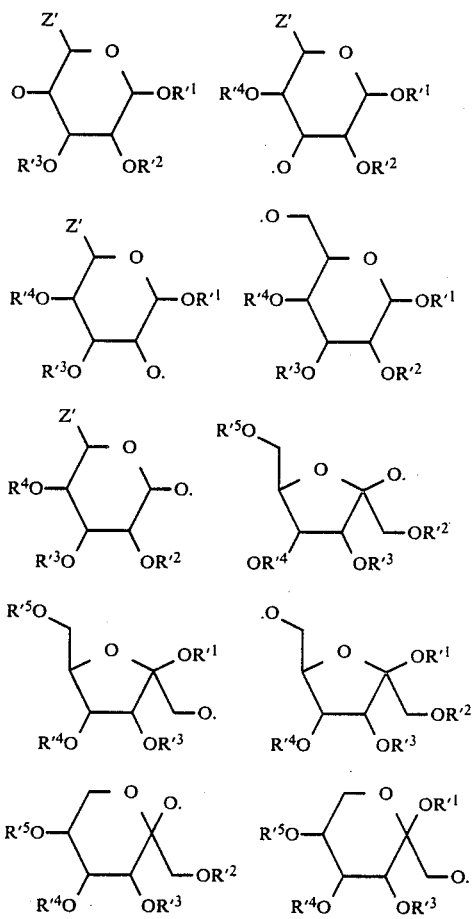

in which the substituents R' and Z' have (independently) the same significance as Z and the corresponding R substituents in formula I. In this case, the basic hydrophilic moiety is derived from a diholoside.

Another object of the present invention is a process for the preparation of the new compounds as defined above.

Said process is essentially characterized by the fact that the starting material is said polyol or aminopolyol, or a derivative thereof, including internal ethers or ketals thereof, wherein the hydroxyl groups, or part thereof, are protected, or wherein at least one hydroxyl group is replaced by a leaving group, that said starting material is reacted with a highly fluorinated derivative, in a manner known per se, so as to link the polyol or aminopolyol moiety with the highly fluorinated moiety through a functional junction group, and that the protected groups, when present, are deprotected according to usual methods.

The highly fluorinated derivative may be for example an alcohol, an amine, an anhydride, a mixed anhydride or an acyl chloride.

The leaving group may be for example a halogen (other than fluorine, preferably bromine) or an activated alcohol derivative such as a tosylate, mesylate or triflate group.

Such a derivative with a leaving group will react with the highly fluorinated derivative (in the form of an alcohol or an amine) to form a corresponding ether or amine bond.

When the highly fluorinated group is present in the form of a $R_F$—W— group as defined above, the process of the invention is essentially characterized by the fact that the hydrophilic starting material, as defined above, is reacted with a member of the group consisting of:

(a) an alcohol $R_F$—W—OH, where $R_F$—W— is other than acyl, (b) an amine $R_F$—W—NH(R''), where $R_F$—W— is other than acyl, R'' being —H, $C_1$-$C_{18}$ alkyl, $C_2$-$C_{18}$ unsaturated alkyl or $R_F$—W— and where the hydrophilic starting material has a leaving group, (c) a mixed anhydride $R_F$—W—O—CO—OAlk, Alk being lower alkyl, or an acyl chloride $R_F$—W—Cl where $R_F$ is an acyl and where the starting material is an aminopolyol, and (d) an acylchloride $R_F$—W—Cl, where $R_F$—W— is acyl, so as to obtain:

in cases (a) and (d) respectively an ether or ester of the type $R_F$—W—O—(hydrophilic moiety), and in cases (b) and (c) respectively an amine or amide of the type $R_F$—W—N(R'')—(hydrophilic moiety), and by the fact that the protected groups, when present, are subjected to a deprotection reaction according to known methods.

In case (c), when the starting material is reacted with the acylchloride, the —OH groups must be protected in order to obtain the desired amide.

The invention relates particularly to a process for the preparation of compounds of formula I, wherein:

either the starting material is a compound similar to a compound of formula I, but having no highly fluorinated group, and $R_5$ and $R_6$, when present, are different from —H, and wherein the —OH groups of said starting material which are not desired to be substituted are temporarily protected, said starting material is reacted with an acylchloride $R_F$—W—Cl (when $R_F$—W— is an acyl) or with a compound $R_F$—W—Z' (when $R_F$—W— is different from an acyl), where Z' is —OH or a leaving group, so as to obtain respectively the corresponding ester or ether of formula I, and then the protected groups are subjected to a deprotection reaction;

or the starting material is a compound similar to a compound of formula I, but having no highly fluorinated group, wherein at least one of the —$OR_1$, —$OR_2$, —$OR_3$, —$OR_4$, —$OR_7$, —$OR_9$, $OR_{10}$ or —$NR_5R_6$ groups is replaced by a leaving group, and wherein the —OH groups are protected, said starting material is reacted with an alcohol $R_F$—W—OH or amine $R_F$—W—NHR'', wherein $R_F$—W— is other than acyl and R'' is —H, $C_1$—$C_{18}$ alkyl, $C_2$-$C_{18}$ unsaturated alkyl, or $R_F$—W—, so as to obtain a corresponding compound of formula I wherein the leaving group of the starting material is replaced respectively by a —O—W—$R_F$ or —N(R")—W—R_F substituent, and then the protected groups are subjected to a deprotection reaction;

or the starting material is a compound similar to a compound of formula I, having a —NR$_5$R$_6$ group, but having no highly fluorinated group, wherein at least one of R$_5$ and R$_6$ is —H, said starting material is reacted with a mixed anhydride of the formula R$_F$—W—O—CO—OAlk (R$_F$—W— being an acyl and Alk being lower alkyl), so as to obtain a corresponding amide of formula I having a —NR$_5$(R$_F$W), —NR$_6$(R$_F$W) or —N(R$_F$W)$_2$ group.

When the resulting product of formula I is an ether having a R$_F$—W—O— group, W representing an unsaturated alkyl of the formula —(CH$_2$)$_p$—CH=CH—(CH$_2$)$_q$—, said product may be converted into another compound of formula I by reduction of the double bond, according to known methods. The corresponding compound thus obtained is one where W represents —(CH$_2$)—$_{p+q+2}$.

For preparing a compound of formula I, where W is —(CH$_2$)$_p$—CH=CH—(CH$_2$)$_q$—, with $q=0$, the starting material is etherified with the alcohol HO—(CH$_2$)$_p$—CH=CH$_2$. By reacting said alcohol with a halide R$_F$—W—Hal (wherein Hal is halogen other than fluorine, for example iodine), there is obtained a corresponding ether of the type —O—(CH$_2$)$_p$—CH=CH—R$_F$ which may be reduced, if desired, to the corresponding ether of the type —O—(CH$_2$)$_{p+2}$—R$_F$.

In a general manner, the —OH groups to be protected in the starting material can be protected in the form of esters. When the starting material has a leaving groups (such as bromine), in the anomeric position and the next carbon atom has a hydroxyl groups protected as an ester (for example an ester of the type Alk—CO—O—, Alk being lower alkyl), the reaction of the alcohol R$_F$—W—OH on the starting material gives as an intermediate product an ortho ester according to the reaction:

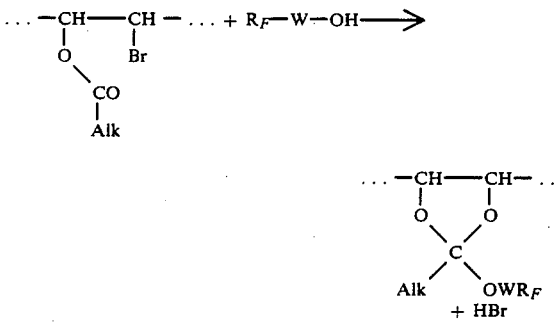

By rearrangement in the presence of HgBr$_2$ in anhydrous medium, the ortho-ester is then converted into the corresponding —OWR$_F$ ether of the partial formula:

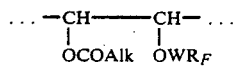

The obtained compounds which contain temporarily protected hydroxyl groups may be subjected to a deprotection reaction according to the known techniques.

When the starting material has a leaving group wich is a halogen (other than fluorine, for example bromine), the reaction with the alcohol R$_F$—W—OH, for obtaining an ether bond, may be carried out according to the known method of Koenigs-Knorr (or the known variations thereof) in the presence of a silver salt, such as silver carbonate, or of silver oxide. In this case, the hydroxyl groups which are not to be etherified are protected in the form of esters.

Moreover, when the starting material contains cis vic-glycol groups, the hydroxyl groups of said vic-glycols may be temporarily protected in the form of acetonides, according to the known methods. The isolated hydroxyl groups remain unprotected and may then be etherified or esterified by a R$_F$W— group.

Of course, the starting materials may be used in the form of the internal ethers (anhydrides) or ketals of the products of formula I.

The invention also relates to the use of the highly fluorinated compounds as defined above, including the compounds of formula I, and mixtures thereof, as surfactants or co-surfactants.

Said surfactants may be used especially in biomedical preparations as described above.

The invention also relates to compositions in the form of, solutions, dispersions, gels, emulsions and microemulsions in water or any other polar solvent, containing non polar substances and compounds such as oils, hydrocarbonated or not, and incorporating at least one hydrophilic and fluorinated compound as defined above, and optionally another surfactant.

The said non polar substances, compounds or oils may be highly fluorinated or perfluorinated.

In such compositions, said highly fluorinated or perfluorinated compound or substances, with molecular masses between about 400 and 700, may be chosen especially among at least of the following: the bis(F-alkyl)-1,2-ethenes and more particularly the bis(F-butyl)-1,2-ethenes, the F-isopropyl-1-F-hexyl-2-ethenes and the bis(F-hexyl)-1,2-ethenes, the perfluorodecalins, the perfluoro-methyldecalins, the perfluoro-dimethyldecalins, the perfluorodimethyladamantanes, the perfluorotrimethylbicyclo-/3,3,1/nonanes and their homologues, ethers of formula (CF$_3$)CFO(CF$_2$CF$_2$) OCF(CF$_3$)$_2$, (CF$_3$)$_2$CFO(CF$_2$CF$_2$)$_3$OCF(CF$_3$)$_2$, (CF$_3$)$_2$CFO(CF$_2$CF$_2$)$_2$F, (CF$_3$)$_2$CFO(CF$_2$CF$_2$)$_3$F, F[CF (CF$_3$)CF$_2$O]$_2$ CHFCF$_3$, (C$_6$F$_{13}$)$_2$O, the amines N(C$_3$F$_7$)$_3$, N(C$_4$F$_9$)$_3$, the perfluoromethylquinolidines and perfluoroisoquinolidines, the halogen derivatives C$_6$F$_{13}$Br, C$_8$F$_{17}$Br, C$_6$F$_{13}$CBr$_2$CH$_2$Br, 1-bromoheptadecafluoro-4-isopropylcyclohexane and analogues, it being understood that the compounds can be used separately or in the form of mixtures.

Such compositions are more particularly used as gas carriers, and in particular for oxygen, in living surroundings, for human and veterinary medical applications, in particular as blood substitutes, contrast agents, means to treat cerebral and cardiac ischemia, for the preservation of organs, tissues, embryos, semen, medium usable in cardiovascular therapy and surgery, for example as a cardioplegic, reperfusion, or coronary angioplasty solution, medium usable as adjuvant for radiotherapy or chemotherapy of cancer, or medium usable as medicinal vehicle.

Typically, the compositions of the present invention consist essentially of 5–70% (vol/vol) of said non polar compound, and 0.5–12% (vol/vol) of at least one surfactant, and the remainder being the solvent, e.g. water.

The surfactant consists of at least one of the polyhydroxylated and highly fluorinated surfactants of the present invention, optionally in combination with conventional surfactants, said fluorinated surfactants representing, by volume, from 5% to 100% of the total volume of surfactants.

The compositions may also comprise usual additives, including inorganic salts, generally in the form of buffers, which allow to adjust the pH and to obtain an isotonic composition.

Among the polyhydroxylated highly fluorinated surfactant compounds of the invention, there may be used especially one of the following:

the 2'-(F-hexyl)-ethyl-β-D-glucopyranoside,
the 2'-(F-hexyl)-ethyl-α-D-glucopyranoside,
the 2'-(F-octyl)-ethyl-β-D-glucopyranoside,
the 2'-(F-octyl)-ethyl-α-D-glucopyranoside,
the 2'-(F-hexyl)-ethyl-β-D-galactopyranoside,
the 2'-(F-hexyl)-ethyl-α-D-galactopyranoside,
the 3'-(F-hexyl)-propyl-β-D-xylopyranoside,
the 3'-(F-hexyl)-propyl-β-L-rhamnopyranoside,
the 2'-(F-butyl)-ethyl-4-O-(α-D-glucopyranosyl)-β-D-glucopyranoside, or 2'-(F-butyl)-ethyl-β-D-maltopyranoside,
the 2'-(F-hexyl)-ethyl-4-O-(α-D-glucopyranosyl)-β-D-glucopyranoside, or 2'-(F-hexyl)-ethyl-β-D-maltopyranoside,
the 2'-(F-hexyl)-ethyl-4-O-(α-D-glucopyranosyl)-α-D-glucopyranoside, or 2'-(F-hexyl)-ethyl-α-D-maltopyranoside,
the 2'-(F-octyl)-ethyl-4-O-(α-D-glucopyranosyl)-β-D-glucopyranoside, or 2'-(F-octyl)-ethyl-β-D-maltopyranoside,
the 2'-(F-octyl)-ethyl-4-O-(α-D-glucopyranosyl)-α-D-glucopyranoside, or 2'-(F-octyl)-ethyl-α-D-maltopyranoside,
the 3'-(F-butyl)-propyl-4-O-(α-D-glucopyranosyl)-β-D-glucopyranoside or 3'-(F-butyl)-propyl-β-D-maltopyranoside,
the 3'-(F-hexyl)-propyl-4-O-(α-D-glucopyranosyl)-β-D-glucopyranoside or 3'-(F-hexyl)-propyl-β-D-maltopyranoside,
the 3'-(F-octyl)-propyl-4-O-(α-D-glucopyranosyl)-β-D-glucopyranoside or 3'-(F-octyl)-propyl-β-D-maltopyranoside,
the 11'-(F-butyl)-undecyl-4-O-(α-D-glucopyranosyl)-β-D-glucopyranoside or 11'-(F-butyl)-undecyl-β-D-maltopyranoside,
the 11'-(F-hexyl)-undecyl-4-O-(α-D-glucopyranosyl)-β-D-glucopyranoside or 11'-(F-hexyl)-undecyl-β-D-maltopyranoside,
the 11'-(F-octyl)-undecyl-4-O-(α-D-glucopyranosyl)-β-D-glucopyranoside or 11'-(F-octyl)-undecyl-β-D-maltopyranoside,
the 2'-(F-hexyl)-ethyl-4-O-(β-D-galactopyranosyl)-β-D-glucopyranoside or 2'-(F-hexyl)-ethyl-β-D-lactopyranoside,
the 2'-(F-octyl)-ethyl-4-O-(β-D-galactopyranosyl)-β-D-glucopyranoside or 2'-(F-octyl)-ethyl-β-D-lactopyranoside,
the 2'-(F-octyl)-ethyl-4-O-(β-D-glucopyranosyl)-β-D-glucopyranoside or 2'-(F-octyl)-ethyl-β-D-cellobiopyranoside,
the 6-O-|3'-(F-butyl)-2'-propenyl|-D-galactose,
the 6-O-|3'-(F-hexyl)-2'-propenyl|-D-galactose,
the 6-O-|3'-(F-octyl)-2'-propenyl|-D-galactose,
the 3-O-|3'-(F-butyl)-2'-propenyl|-D-glucose,
the 3-O-|3'-(F-hexyl)-2'-propenyl|-D-glucose,
the 3-O-|3'-(F-octyl)-2'-propenyl|-D-glucose,
the 6-O-|3'-(F-butyl)-propyl|-D-galactose,
the 6-O-|3'-(F-hexyl)-propyl|-D-galactose,
the 6-O-|3'-(F-octyl)-propyl|-D-galactose,
the 3-O-|3'-(F-butyl)-propyl|-D-glucose,
the 3-O-|3'-(F-hexyl)-propyl|-D-glucose,
the 3-O-|3'-(F-octyl)-propyl|-D-glucose,
the 3-O-|3'-(F-pentyl)-propanoyl|-D-glucose,
the 3-O-|3'-(F-heptyl)-propanoyl|-D-glucose,
the 3-O-|3'-(F-octyl)-propanoyl|-D-glucose,
the 6-O-|3'-(F-pentyl)-propanoyl|-D-galactose,
the 6-O-|3'-(F-heptyl)-propanoyl|-D-galactose,
the 6-O-|3'-(F-octyl)-propanoyl|-D-galactose,
the 3-O-|11'-(F-hexyl)-undecanoyl|-D-glucose,
the 6-O-|11'-(F-butyl)-undecanoyl|-D-galactose,
the 6-O-|11'-(F-hexyl)-undecanoyl|-D-galactose,
the 6-O-|11'-(F-octyl)-undecanoyl|-D-galactose,
the 3-O-|3'-(F-octyl)-propanoyl|-D-xylose,
the 6-O-|3'-(F-octyl)-propanoyl|-D-fructose,
the 1-O-|3'-(F-octyl)-propanoyl|-D-fructose,
the β-D-fructofuranosyl-6-O-|3'-(F-octyl)-propanoyl|-α-D-glucopyranoside or 6-O-|3'-(F-octyl)-propanoyl|-sucrose,
the 6-O-|3'-(F-octyl)-propanoyl|-β-D-fructopyranosyl 6-O-|3'-(F-octyl)-propanoyl|-α-D-glucopyranoside, or 6,6'-di-|3'-(F-octyl)-propanoyl|-sucrose,
the 5-O-|3'-(F-butyl)-2'-propenyl|-xylitol,
the 5-O-|3'-(F-hexyl)-2'-propenyl|-xylitol,
the 5-O-|3'-(F-octyl)-2'-propenyl|-xylitol,
the 5-O-|3'-(F-butyl)-propyl|-xylitol,
the 5-O-|3'-(F-pentyl)-propanoyl|-xylitol,
the 5-O-|3'-(F-heptyl)-propanoyl|-xylitol,
the 5-O-|3'-(F-octyl)-propanoyl|-xylitol,
the 5-O-|11'-(F-hexyl)-undecanoyl|-xylitol,
the 3,4-di-O-|3'-(F-octyl)-propanoyl|-D-mannitol,
the 2-O-|3'-(F-pentyl)-propanoyl|-1,4:3,6-dianhydro-D-mannitol,
the 2-O-|3'-(F-octyl)-propanoyl|-1,4:3,6-dianhydro-D-mannitol,
the 2-O-|3'-(F-octyl)-propanoyl|-1,4:3,6-dianhydro-D-sorbitol,
the 5-O-|3'-(F-octyl)-propanoyl|-1,4:3,6-dianhydro-D-sorbitol,
the 6-O-|3'-(F-octyl)-propanoyl|-1,4-D-sorbitan,
the 6-O-|11'-(F-octyl)-undecanoyl|-1,4-D-sorbitan,
the |3'-(F-pentyl)-propanoyl|-N-methyl-D-glucamide,
the |3'-(F-heptyl)-propanoyl|-N-methyl-D-glucamide,
the |3'-(F-octyl)-propanoyl|-N-methyl-D-glucamide
the 2-deoxy-2-|3'-(F-octyl)-propanamido|-D-glucose,
the 2-deoxy-2-|3'-(F-octyl)-propanamido|-D-glucitol,
the 3-O-|3'-(F-octyl)-propanoyl|-myo-inositol.

EXAMPLES

The following examples illustrate these diverse possibilities, being understood that the compounds described are only some of those which can be obtained, and that they can be obtained also by yet other methods than those listed hereunder, which are only some of the various possible preparation methods. Likewise these processes can apply just as well to optically pure compounds as to mixtures of stereoisomers.

EXAMPLE 1

2'-(F-hexyl)-ethyl-D-glucopyranoside, 3α and 3β

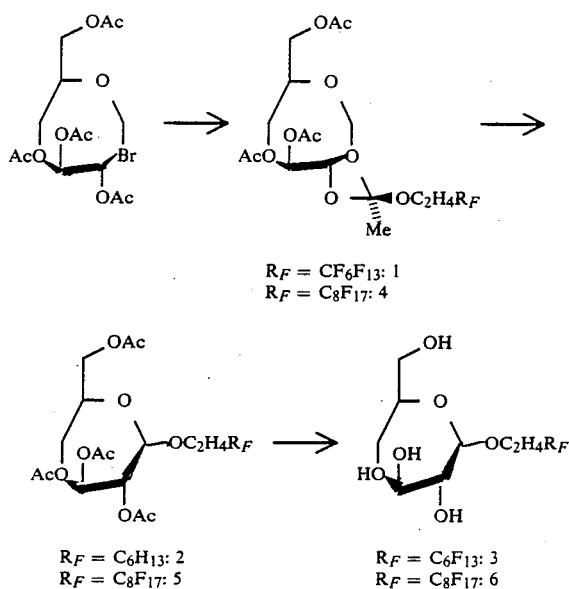

$R_F = C_6F_{13}$: 1
$R_F = C_8F_{17}$: 4

$R_F = C_6H_{13}$: 2
$R_F = C_8F_{17}$: 5

$R_F = C_6F_{13}$: 3
$R_F = C_8F_{17}$: 6

Step 1: Preparation of the orthoester, 1

8.22 g (20 mmol) of tetra-O-acetyl-α-D-glucopyranosyl bromide dissolved in 20 ml of anhydrous nitromethane are treated under argon with 14.9 g (41 mmol) of 2-(F-hexyl)-ethanol and 4 ml of anhydrous 2,6-lutidine at 25° C. After the tetra-O-acetyl-α-D-glucopyranosyl bromide has disappeared (as shown by thin layer chromatographic monitoring), a 2M solution of silver nitrate (16 ml) is added, followed by 20 ml of water and 50 ml of acetone. The precipitate is filtered over celite and washed three times with 50 ml of chloroform. The organic phase is separated, washed with water and dried over $Na_2SO_4$. After filtration, the chloroform is distilled, then the excess of perfluoroalkylated alcohol is distilled under 0.02 mm Hg at 70° C. The orthoester 1 (11 g, 79%) is recrystallized from a hexane/diisopropylether mixture.

m.p. = 108°–9° C.—white needles $|\alpha|_D^{23} = +21.7°$ (c 1.2 $CHCl_3$). C found(calculated): 38.32 (38.05); H: 3.09 (3.34); F: 35.89 (35.57).

$^1H$ (TMS): δ(anomeric H)=5.7 ppm (J=5.3 Hz); δ($CH_3$ orthoester)=1.71 ppm $^{19}F$ ($CCl_3F$): δ($CF_2CH_2$)= −114 ppm $^{13}C$ (TMS): δ(quaternary C)=121 ppm; δ(anomeric C)=97 ppm; δ($OCH_2CH_2$)=56 ppm; δ($OCH_2CH_2$)=31 ppm.

Step 3.2: Preparation of 2'-(F-hexyl)-ethyl-α-D-glucopyranoside, 3α

0.81 g (1.2 mmol) of 2'-(F-hexyl)-ethyl-2,3,4,6-tetra-O-acetyl-α-D-glucopyranoside 2α is stirred with 5.2 ml of an $MeOH/Et_3N/H_2O$ mixture (2/1/1). After evaporation and chromatography over silica (AcOEt/MeOH 8/1), 509 mg (81%) of 3α are obtained.

$|\alpha|_D^{26} = +65.6°$ (c 1 MeOH). C: 32.11 (31.95); H: 2.75 (2.87); F: 46.97 (46.93).

EXAMPLE 2

Preparation of 2'-(F-octyl)-ethyl-D-glucopyranoside, 6α and 6β

The process described for example 1 is repeated, allowing in the first step 22.5 g (48.5 mmol) of 2-(F-octyl)-ethanol to react with 9.95 g (24.2 mmol) of tetra-O-acetyl-α-D-glucopyranosyl bromide. In this first step 16.4 g (85%) of the orthoester 4, recrystallized in diisopropyl ether, are obtained.

m.p. = 120°–1° C. $|\alpha|_D^{24} = +13°$ (c 1.6 $CHCl_3$).
C: 36.57 (36.29); H: 3.04 (2.92); F: 39.95 (40.65).
$^1H$ (TMS): δ(anomeric H)=5.71 ppm (J=4.8 Hz); δ($CH_3$ orthoester)=1.74 ppm.
$^{19}F$ ($CCl_3F$): δ($CF_2CH_2$)= −114 ppm.
$^{13}C$ (TMS): δ(quaternary C)=121 ppm; δ(anomeric C)=97 ppm; δ($OCH_2CH_2$)=56 ppm; δ($OCH_2CH_2$)=31 ppm.

In the second step, using 15.2 g (19.1 mmol) of this intermediate product 4, we obtained, after chromatography and several recrystallizations, 3.3 g (22%) of 2'-(F-octyl)-ethyl-2,3,4,6-tetra-O-acetyl-β-D-glucopyranoside 5β.

m.p. = 122°–3° C. $|\alpha|_D^{23} = -6.7°$ (c 2 $CHCl_3$).
C: 36.60 (36.29); H: 2.99 (2.92); F: 40.00 (40.65).
$^1H$ (TMS): δ(anomeric H)=4.55 ppm (J=8 Hz).
$^{19}F$ ($CCl_3F$): δ($CF_2CH_2$)= −114 ppm.
$^{13}C$ (TMS): δ(anomeric C)=101 ppm; δ($OCH_2CH_2$)=62 ppm; δ($OCH_2CH_2$)=31.7 ppm.

and 2.17 g (14%) of 2'-(F-octyl)-ethyl 2,3,4,6-tetra-O-acetyl-α-D-glucopyranoside 5α.

m.p. = 57°–8° C. $|\alpha|_D^{20} = +66.3°$ (c 0.8 $CHCl_3$).
C: 36.95 (36.29); H: 2.94 (2.92); F: 40.23 (40.65).
$^{19}F$ ($CCl_3F$): δ($CF_2CH_2$)= −114 ppm.
$^{13}C$ (TMS): δ(anomeric C)=96 ppm; δ($OCH_2CH_2$)=61 ppm; δ($OCH_2CH_2$)=31 ppm. Finally, in a third step, starting from 3.06 g (3.85 mmol) of this second intermediate 5β, 2.24 g (93%) of 2'-(F-octyl)-ethyl-β-D-glucopyranoside 6β are obtained.

m.p. = 152°–3° C. $|\alpha|_D^{24} = -12.6°$ (c 1 MeOH).
C: 30.57 (30.69); H: 2.22 (2.41); F: 51.58 (51.57).
$^{19}F$ ($CCl_3F$): δ($CF_2CH_2$)= −114 ppm.
$^{13}C$ (TMS): δ(anomeric C)=104 ppm; δ($OCH_2CH_2$)=62 ppm; δ($OCH_2CH_2$)=32 ppm.

In the same manner, 2.06 g (2.59 mmol) of 5α lead to 1.14 g (70%) of 2'-(F-octyl)-ethyl-α-D-glucopyranoside 6α.

m.p. = 85°–6° C. $|\alpha|^{21}_D = +49.0°$ (c 1.3 MeOH).
C: 30.71 (30.69); H: 2.48 (2.41); F: 51.32 (51.57).
$^{13}C$ (TMS): δ(anomeric C)=100.8 ppm.

EXAMPLE 3

Preparation of 3-O-|3'-(F-octyl)-propanoyl|-D-glucose, 8

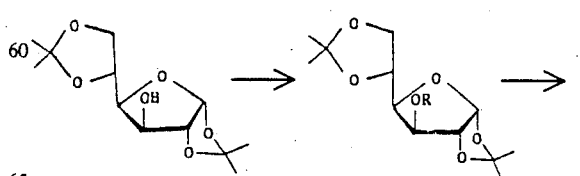

R = $C_8F_{17}C_2H_4CO$: 7
R = $C_6F_{13}(CH_2)_{10}CO$: 9

-continued

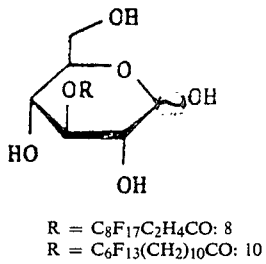

R = C$_8$F$_{17}$C$_2$H$_4$CO: 8
R = C$_6$F$_{13}$(CH$_2$)$_{10}$CO: 10

Step 1: Preparation of 3-O-|3'-(F-octyl)-propanoyl|-1,2:5,6-di-O-isopropylidene-α-D-glucofuranose, 7

To a solution of 7.82 g (30 mmol) of 1,2:5,6-di-O-isopropylidene-α-D-glucofuranose and 3 ml of anhydrous pyridine in 250 ml of anhydrous CHCl$_3$, 15.35 g (30 mmol) of 3'-(F-octyl)-propanoyl chloride are added drop by drop. The solution is stirred overnight at room temperature, the major part of the CHCl$_3$ is then evaporated in vacuo, and ether is added. The organic phase is washed with water until neutrality is reached, then dried over Na$_2$SO$_4$. The solvent is filtered and evaporated, and 20.7 g of glucofuranose 7 (94%) are obtained, which are recrystallized in pentane.

m.p.=67° C.; $|α|_D^{23}$=−15.3° (c 1.3 CHCl$_3$).
C: 36.24 (37.62); H: 3.06 (3.16); F: 43.91 (43.98).
$^1$H (TMS): δ(anomeric H)=5.88 ppm (J=2.5 Hz).
$^{19}$F (CCl$_3$F): δ(C$\underline{F}_2$CH$_2$)=−116 ppm.

Step 2: Preparation of 3-O-|3'-(F-octyl)-propanoyl|-D-glucose, 8

5 g (6.80 mmol) of |3'-(F-octyl)-propanoyl|-1,2:5,6-di-O-isopropylidene-α-D-glucofuranose 7 are agitated for 30 mn at room temperature with a solution of trifluoroacetic acid in water (ratio 9/1 v/v). After evaporation and recrystallization from methanol, 3.65 g (82%) of product 8 are obtained.

m.p.=100°-2° C. $|α|_D^{20}$=+12.8° (c 1.2 DMSO).
C: 30.82 (31.21); H: 2.24 (2.31); F: 49.32 (49.36).
IR (KBr): ν(OH)=3430 cm$^{-1}$; ν(C=O)=1740 cm$^{-1}$.

EXAMPLE 4

Preparation of 3-O-|11'-(F-hexyl)-undecanoyl|-D-glucose, 10

By reaction of 10.89 g (21 mmol) of 11-(F-hexyl)-undecanoyl chloride with 5.92 g (23 mmol) of 1,2:5,6-di-O-isopropylidene-α-D-glucofuranose as in step 1 of example 3, and after chromatography over silica (hexane/AcOEt 3/2), 14 g (90%) of solid 9 are obtained.

m.p.=37° C. $|α|_D^{25}$=−15.1° (c 1.6 CHCl$_3$).
C: 46.86 (46.65); H: 5.30 (5.27); F: 32.98 (33.08).
$^1$H (TMS): δ(anomeric H)=5.86 ppm (J=3.7 Hz).
$^{13}$C (TMS): δ(quaternary C)=112.5 ppm, 109.5 ppm; δ(anomeric C)=105.3 ppm; δ($\underline{C}$H$_2$C$_6$F$_{13}$)=32.1 ppm.

In the second step, 3.3 g (4.4 mmol) of 9 are deacetylated by stirring with 10 ml of a CF$_3$CO$_2$H/H$_2$O (9/1) mixture. 1.6 g (54%) of 10 are obtained by recrystallization from MeOH.

m.p.=108°-10° C. $|α|_D^{26}$=+36.1° (c 1.1 DMSO).
C: 41.41 (41.45); H: 4.72 (4.69); F: 37.13 (37.06).

EXAMPLE 5

Preparation of 2'-(F-hexyl)-ethyl-D-galactopyranoside, 13α and 13β

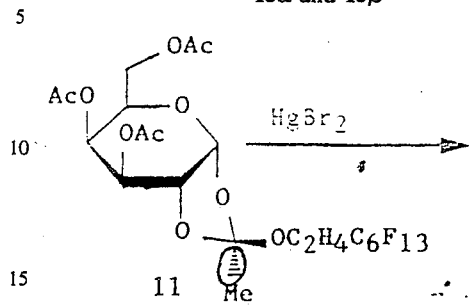

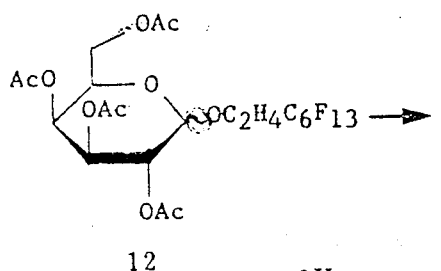

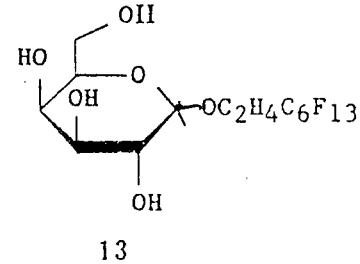

The process described for example 1 is repeated. In the first step 12.4 g (30.2 mmol) of tetra-O-acetyl-α-D-galactopyranosyl bromide are allowed to react with 23.3 g (61.2 mmol) of 2-F-hexyl-ethanol leading, after chromatography (CH$_2$Cl$_2$/AcOEt 6/1), to 13.8 g (66%) of orthoester 11, as a viscous liquid.

$|α|_D^{24}$=+40.4° (c 2.3 CHCl$_3$).
H: 3.39 (3.34).
$^1$H (TMS): δ(anomeric H)=5.8 ppm (J=5.3 Hz); δ(CH$_3$ orthoester)=1.69 ppm.
$^{13}$C (TMS): δ(quaternary C)=121 ppm; δ(anomeric C)=97.9 ppm; δ(O$\underline{C}$H$_2$CH$_2$)=55 ppm; δ(OCH$_2$$\underline{C}$H$_2$)=31.6 ppm.

In a second step 5.4 g (7.78 mmol) of orthoester 11 lead after chromatography over silica (eluant diisopropyl ether) to 1.08 g of liquid galactoside 12α (20%) and 2.72 g of liquid galactoside 12β (50%).

β Anomer $|α|_D^{21}$=−1.9° (c 1.3 CHCl$_3$).
C: 38.49 (38.05); H: 3.38 (3.34); F: 35.08 (35.57).
$^1$H (TMS): δ(anomeric H)=4.52 ppm (J=7.2 Hz).
$^{13}$C (TMS): δ(anomeric C)=101.5 ppm; δ(O$\underline{C}$H$_2$CH$_2$)=62 ppm; δ(OCH$_2$$\underline{C}$H$_2$)=31.6 ppm.

α Anomer $|α|_D^{21}$=+82.4° (c 1.2 CHCl$_3$).
C: 38.21 (38.05); H: 3.43 (3.34); F: 35.07 (35.57).
$^{13}$C (TMS): δ(anomeric C)=96.6 ppm; δ(O$\underline{C}$H$_2$CH$_2$)=60.7 ppm; δ(OCH$_2$$\underline{C}$H$_2$)=31.3 ppm.

Finally in the third step, 2.58 g (3.7 mmol) of galactoside 12β lead to 1.86 g (95%) of 2'-(F-hexyl)-ethyl-β-D-galactopyranoside 13β.

$|\alpha|_D^{25} = -3.5°$ (c 1.1 MeOH).

C: 31.93 (31.95); H: 2.90 (2.87); F: 46.52 (46.93).

$^{13}$C (TMS): δ(anomeric C)=105.2 ppm; δ(OCH$_2$CH$_2$)=62.4 ppm; δ(OCH$_2$C$_{H2}$)=32.4 ppm.

while 950 mg of galactoside 12α yield 575 mg (80%) of 2'-(F-hexyl)-ethyl-α-D-galactopyranoside 13α.

$|\alpha|_D^{25} = +74.8°$ (c 2.2 MeOH).

C: 31.93 (31.95); H: 2.89 (2.87); F: 47.05 (46.93).

$^{13}$C (TMS): δ(anomeric C)=100.9 ppm; δ(OCH$_2$CH$_2$): 61.2 ppm; δ(OCH$_2$C$_{H2}$)=32 ppm.

EXAMPLE 6

Preparation of 6-O-|3'-(F-hexyl)-2'-propenyl|-D-galactose, 15

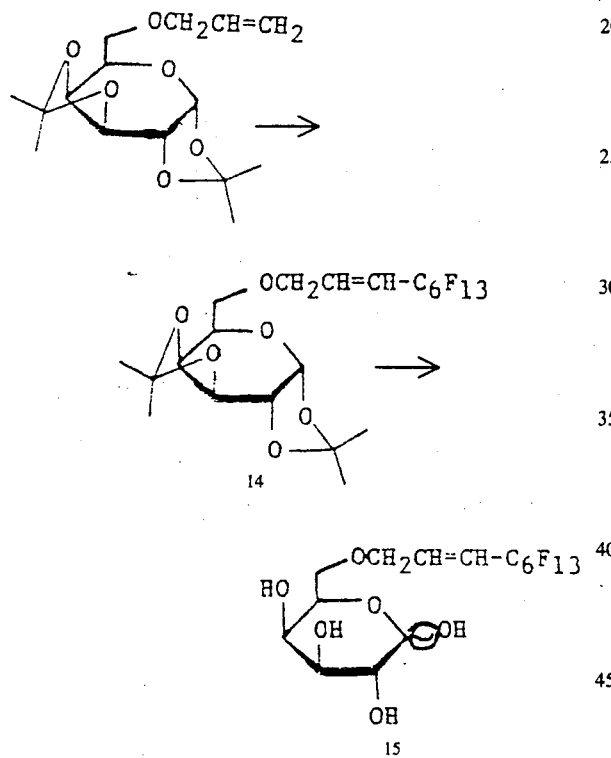

Step 1: Preparation of 6-O-|3'-(F-hexyl)-2'-propenyl|-1,2:3,4-di-O-isopropylidene-α-D-galactopyranose, 14

Under argon, 1.25 g (4.13 mmol) of 6-O-(2'-propenyl)-1,2:3,4-di-O-isopropylidene-α-D-galactopyranose, 100 mg of copper chloride, 5 ml of F-hexyl iodide, 1 ml of ethanolamine and 5 ml of t-butanol are heated to 110° C. for 24 h. After cooling and addition of 20 ml water, the reaction mixture is extracted with ether. After treatment, the viscous liquid obtained is purified by chromatography over silica (eluant hexane/ether 6/4), yielding 2.34 g (91%) of galactopyranoside 14 (cis+trans).

$|\alpha|_D^{21} = -38.1°$ (c=1.4 CHCl$_3$).

C: 41.02 (40.79); H: 3.75 (3.75); F: 40.33 (39.94).

IR (film): ν(C=C)=1685 cm$^{-1}$.

$^1$H (TMS): δ(anomeric H)=5.50 ppm (J=5 Hz); δ(CH=CH)=6.4–5.6 ppm.

$^{19}$F (CCl$_3$F): δ(CF$_2$—C=C cis)=−108 ppm; δ(CF$_2$—C=C trans)=−112 ppm; cis/trans ratio 15/85.

Step 2: Preparation of 6-O-|3'-(F-hexyl)-2'-propenyl|-D-galactose, 15

1 g (1.8 mmol) of the intermediate 14 is agitated for 15 mn at room temperature with a mixture of trifluoroacetic acid and water (9/1 v/v). After concentration of the solution, and chromatography over silica (eluant AcOEt/CH$_3$OH 4/1), 0.82 g (95%) of 6-O-|3'-(F-hexyl)-2'-propenyl|-D-galactose, 15 is recovered.

m.p.=109° C. $|\alpha|_D=+13.2°$ (c 1.4 MeOH).

C: 33.22 (33.47); H: 2.80 (2.81); F: 45.11 (45.88).

IR (KBr): ν(OH)=3420 cm$^{-1}$; ν(C=C)=1685 cm$^{-1}$.

$^{19}$F (CCl$_3$F): δ(CF$_2$C=C cis)=−107 ppm; δ(CF$_2$C=C trans)=−111 ppm; cis/trans ratio 15/85.

EXAMPLE 7

Preparation of 6-O-|3'-(F-hexyl)-propyl|-D-galactose, 17

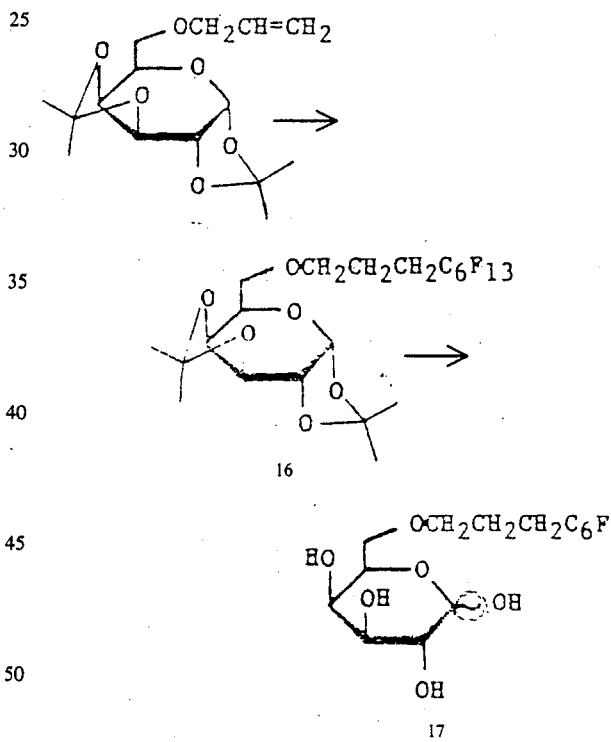

Step 1: Preparation of 6-O-|3'-(F-hexyl)-propyl|-1,2:3,4-di-O-isopropylidene-α-D-galactopyranose, 16

In an autoclave reactor, a mixture of 0.56 g (0.9 mmol) of 6-O|3'-(F-hexyl)-2'-propenyl|-1,2:3,4-di-O-isopropylidene-α-D-galactopyranose 14, 10 ml of methanol and 93 mg of palladium over carbon is submitted to hydrogen pressure (7–8 bars) for 3 days at room temperature. Chromatography over silica yields 0.14 g (25%) of 6-O-|3'-(F-hexyl)-propyl|-1,2:3,4-di-O-isopropylidene-α-D-galactopyranose 16.

$^1$H (TMS): δ(OCH$_2$CH$_2$CH$_2$)=1.65–2.57 ppm (cluster); δ(anomeric H)=5.50 ppm (J=5 Hz).

Step 2: Preparation of 6-O-|3'-(F-hexyl)-propyl|-D-galactose, 17

0.09 g (0.14 mmol) of the intermediate 16 is treated with a mixture of trifluoroacetic acid and water (9/1 v/v) for 15 mn at room temperature. After evaporation of the solvent and chromatography, 0.07 g (90%) of 6-O-|3'-(F-hexyl)propyl|-D-galactose, 17 is obtained.

m.p. = 105° C.

IR (KBr): $\nu$(OH) = 3380 cm$^{-1}$.

$^{19}$F (CCl$_3$F): $\delta$(C$\underline{F}_2$CH$_2$) = −113.7 ppm.

EXAMPLE 8

Preparation of 6-O-|3'-(F-octyl)-propanoyl|-D-galactose, 19

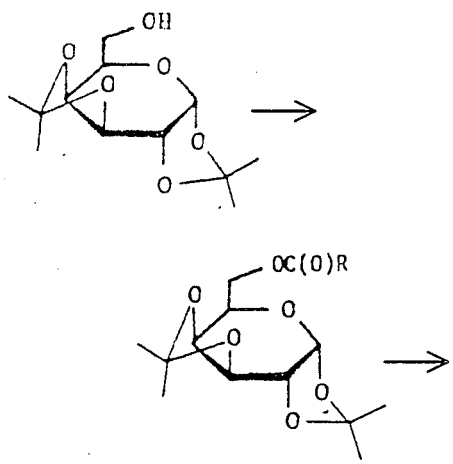

R = C$_8$F$_{17}$C$_2$H$_4$: 18
C$_4$F$_9$(CH$_2$)$_{10}$: 20
C$_6$F$_{13}$(CH$_2$)$_{10}$: 22

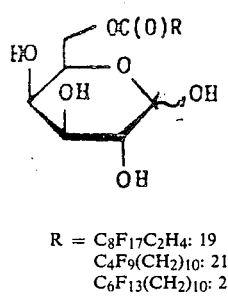

R = C$_8$F$_{17}$C$_2$H$_4$: 19
C$_4$F$_9$(CH$_2$)$_{10}$: 21
C$_6$F$_{13}$(CH$_2$)$_{10}$: 23

The process described in example 3 is repeated with, in the first step, 1,2:3,4-di-O-isopropylidene-α-D-galactopyranose instead of 1,2:5,6-di-O-isopropylidene-α-D-glucofuranose. 7.21 g (27.7 mmol) of the former and 14.20 g (27.8 mmol) of 3'-(F-octyl)-propanoyl chloride yield 18.6 g (91%) of 6-O-|3'-(F-octyl)-propanoyl|-1,2:3,4-di-O-isopropylidene-α-D-galactopyranose, 18.

m.p. = 90°–90.5° C. $|\alpha|_D^{22}$ = −20.1° (c 1.1 CHCl$_3$).

C: 37.88 (37.62); H: 3.03 (3.16); F: 45.19 (43.98).

$^1$H (TMS): $\delta$(anomeric H) = 5.53 ppm (J = 5.6 Hz).

$^{19}$F (CCl$_3$F): $\delta$(C$\underline{F}_2$CH$_2$) = −115 ppm.

In the second step, using 5.04 g (6.87 mmol) of this intermediate 18 and 25 ml of a mixture of CF$_3$COOH and H$_2$O (9/1), 4.44 g (99%) of 6-O-|3'-(F-octyl)-propanoyl|-D-galactose, 19, are obtained:

m.p. = 165°–6° C. $|\alpha|_D^{20}$ = +36.2° (c 1.2 DMSO).

C = 31.56 (31.21); H: 2.23 (2.31); F: 48.28 (49.36).

IR (KBr): $\nu$(OH) = 3430 cm$^{-1}$; $\nu$(C=O) = 1740 cm$^{-1}$.

EXAMPLE 9

Preparation of 6-O-|11'-(F-butyl)-undecanoyl|-D-galactose, 21

As in step 1 of example 8, 10 g (23 mmol) of 11-(F-butyl)-undecanoyl chloride are allowed to react with 6.62 g (25 mmol) of 1,2:3,4-di-O-isopropylidene-α-D-galactopyranose to yield, after chromatography over silica (hexane/AcOEt 3/2), 14.1 g (92%) of liquid 20:

$|\alpha|_D^{25}$ = −21.8° (c 2 CHCl$_3$).

C: 50.10 (50.15); H: 6.13 (6.08); F: 26.33 (26.44).

$^1$H (TMS): $\delta$(anomeric H) = 5.53 ppm (J = 4.7 Hz).

$^{13}$C (TMS): $\delta$(quaternary C) = 109.8 ppm, 108.9 ppm; $\delta$(anomeric C) = 96.5 ppm; $\delta$($\underline{C}$H$_2$C$_4$F$_9$) = 30.9 ppm.

In the second step, 3.4 g (5.26 mmol) of 20 stirred with 10 ml of CF$_3$CO$_2$H/H$_2$O mixture (9/1) give, after treatment and recrystallization from MeOH, 1.5 g (50%) of 21:

m.p. = 122° C. $|\alpha|_D^{26}$ = +37.6° (c 1 DMSO).

C: (44.53); H: (5.52); F: (30.18).

IR (KBr): $\nu$(C=O) = 1725 cm$^{-1}$.

EXAMPLE 10

Preparation of 6-O-|11'-(F-hexyl)-undecanoyl|-D-galactose, 23

Reaction as in step 1 of example 8 of 11.47 g (21 mmol) of 11-(F-hexyl)-undecanoyl chloride with 5.72 g (22 mmol) of 1,2:3,4-di-O-isopropylidene-α-D-galactopyranose leads, after treatment and chromatography over silica (hexane/AcOEt 3/2), to 15.7 g (96%) of the intermediate 22.

m.p. = 33° C. $|\alpha|_D^{25}$ = −18.4° (c 1.5 CHCl$_3$).

C: 46.94 (46.65); H: 5.13 (5.27); F: 32.99 (33.08).

$^1$H (TMS): $\delta$(anomeric H) = 5.53 ppm (J = 5 Hz).

In step 2, 3.45 g (4.62 mmol) of 22 treated with a CF$_3$CO$_2$H/H$_2$O mixture give after recrystallization from MeOH 2.1 g (68%) of 23.

m.p. = 128° C. $|\alpha|_D^{26}$ = +35.0° (c 1.1 DMSO).

C: 41.62 (41.45); H: 4.69 (4.69); F: 37.09 (37.06).

IR (KBr): $\nu$(C=O) = 1725 cm$^{-1}$.

$^{13}$C (TMS): $\delta$(C=O) = 174.1 ppm.

EXAMPLE 11

Preparation of 2'-(F-hexyl)-ethyl 4-O-(α-D-glucopyranosyl)-β (or α)-D-glucopyranoside (or 2'-(F-hexyl)-ethyl-β(or α)-D-maltopyranoside), 26α and 26β

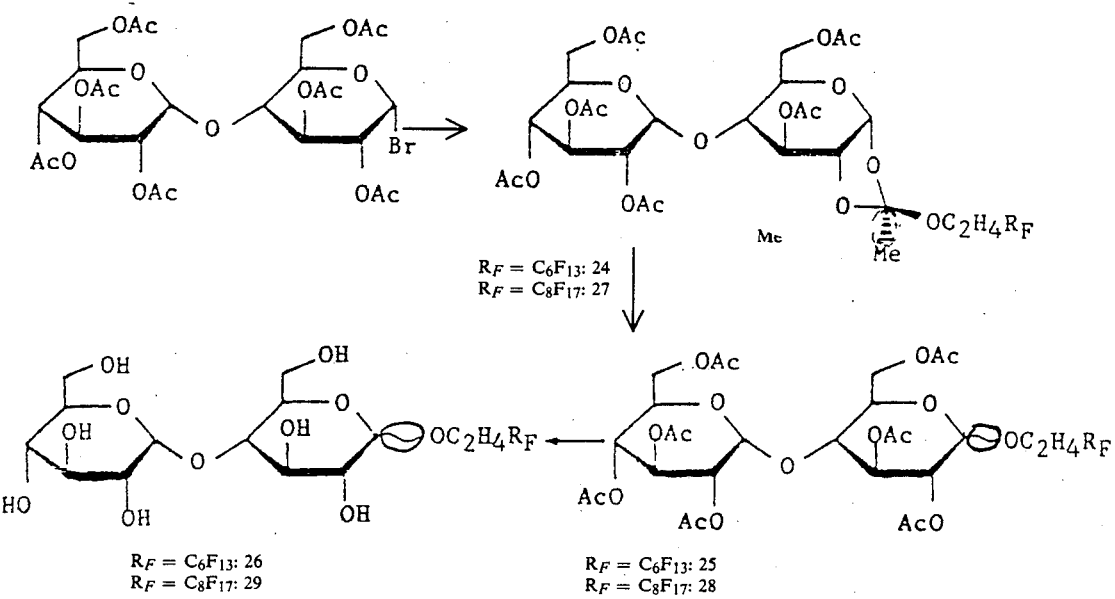

$R_F = C_6F_{13}$: 24
$R_F = C_8F_{17}$: 27

$R_F = C_6F_{13}$: 26
$R_F = C_8F_{17}$: 29

$R_F = C_6F_{13}$: 25
$R_F = C_8F_{17}$: 28

The process described in example 1 is repeated. In step 1, 26 g (37.2 mmol) of hepta-O-acetyl-α-D-maltopyranosyl bromide are allowed to react with 22.7 g (62.3 mmol) of 2-(F-hexyl)-ethanol, yielding after chromatography (hexane/AcOEt 1/1) 29 g (79%) of the orthoester 24.

m.p.=101°-2° C. $|α|_D^{20}= +61.7°$ (c 1.7 CHCl$_3$).
C: 41.46 (41.56); H: 4.06 (4.00); F: 24.22 (25.13).
$^1$H (TMS): δ(anomeric H-1)=5.71 ppm (J=4.8 Hz); δ(CH$_3$ orthoester)=1.77 ppm
$^{19}$F (CCl$_3$F): δ(CF$_2$CH$_2$)= −114 ppm.
$^{13}$C (TMS): δ(quaternary C)=122 ppm; δ(anomeric C-1)=97 ppm; δ(anomeric C-1')=95 ppm.

In step 2, 25 g (25.5 mmol) of orthoester 24 lead to 21 g (84%) of maltoside 25α and 25β. The maltoside 25β is purified by recrystallization from MeOH:

m.p.=132°-5° C. $|α|_D^{21}= +38.0°$ (c 1.2 CHCl$_3$).
C: 41.74 (41.56); H: 4.00 (4.00); F: 24.75 (25.13).
$^1$H (TMS): δ(anomeric H-1')=5.35 ppm (J=5.4 Hz).
$^{19}$F (CCl$_3$F): δ(CF$_2$CH$_2$)= −113 ppm.
$^{13}$C (TMS): δ(anomeric C-1)=100.5 ppm; δ(anomeric C-1')=96 ppm.

In step 3, 7.5 g (7.6 mmol) of maltoside 25β are deacetylated, leading after chromatography to 4.5 g (86%) of 2'-(F-hexyl)-ethyl-4-O-(α-D-glucopyranosyl)-β-D-glucopyranoside, 26β.

$|α|_D^{26}= +30.8°$ (c 1.1 H$_2$O).
C: 34.76 (34.90); H: 3.56 (3.66); F: 35.50 (35.88).
$^1$H (TMS): δ(anomeric H-1')=5.18 ppm (J=3.2 Hz); δ(anomeric H-1)=4.35 ppm (J=8 Hz).
$^{19}$F (CCl$_3$F): δ(CF$_2$CH$_2$)= −114 ppm.
$^{13}$C (TMS): δ(anomeric C-1)=104.6 ppm; δ(anomeric C-1')=103 ppm.

Similar treatment of a mixture of 25α and 25β maltopyranoside gives, after separation by HPLC (reversed phase, eluant MeOH/H$_2$O 65/35), the 2'-(F-hexyl)-ethyl-α-D-maltopyranoside, 26α.

$|α|_D= +78.8°$ (c 1.5 H$_2$O).
C: 34.67 (34.90); H: 3.80 (3.66); F: 35.05 (35.88).
$^{13}$C (TMS): δ(anomeric C-1)=100.7 ppm; δ(anomeric C-1')=103.1 ppm.

EXAMPLE 12

Preparation of 2'-(F-octyl)-ethyl-4-O-(α-D-glucopyranosyl)-α(β)-D-glucopyranoside (or 2'-(F-octyl)-ethyl-α(β)-D-maltopyranoside), 29α and 29β

By the same process as that described in example 1, 32 g (45.8 mmol) of hepta-O-acetyl-α-D-maltopyranosyl bromide treated with 35 g (75.4 mmol) of 2-F-octyl-ethanol lead after chromatography over silica (eluant hexane/AcOEt 1/1) to 39 g (79%) of orthoester 27.

m.p.=95°-6° C. $|α|_D^{23}= +55.3°$ (c 2 CHCl$_3$).
C: 39.91 (39.94); H: 3.62 (3.63); F: 29.62 (29.83).
$^1$H (TMS): δ(CH$_3$ orthoester)=1.77 ppm.
$^{13}$C (TMS): δ(quaternary C)=121.7 ppm; δ(anomeric C-1)=97 ppm; δ(anomeric C-1')=95.2 ppm.

In step 2, refluxing 36.5 g (33.7 mmol) of orthoester 27 with 0.58 g of HgBr$_2$ in anhydrous nitromethane gives, after recrystallization of the crude reaction product, 13 g (35%) of 2'-(F-octyl)-ethyl-hepta-O-acetyl-β-D-maltopyranoside 28β.

m.p.=154°-5° C. $|α|_D^{24}= +33.8°$ (c 1.2 CHCl$_3$).
C: 39.86 (39.94); H: 3.59 (3.63); F: 29.42 (29.83).
$^{13}$C (TMS): δ(anomeric C-1)=100.5 ppm; δ(anomeric C-1')=95.7 ppm.

In step 3, deacetylation of 6.07 g (5.61 mmol) of 2'-(F-octyl)-ethyl-hepta-O-acetyl-β-D-maltopyranoside 28β yields 4.16 g (94%) of 2'-(F-octyl)-ethyl-β-D-maltopyranoside 29β.

m.p.=175° C. $|α|_D^{26}= +30.4°$ (c 1.1 MeOH).
C: 33.37 (33.52); H: 2.93 (3.20); F: 39.75 (40.96).
$^{13}$C (TMS): δ(anomeric C-1)=104.5 ppm; δ(anomeric C-1')=102.9 ppm.

It is also possible to prepare a mixture of 29α and 29β. By reaction of 41.3 g (59 mmol) of hepta-O-acetyl-α-D-maltopyranosyl bromide with 59 g of 2-F-octyl ethanol, after treatment 56.5 g (88%) of orthoester 27 are obtained by recrystallization from diisopropyl ether.

In step 2, 27 is converted as above to 28 ($\alpha+\beta$) which is deacetylated. The crude reaction mixture is concentrated and purified by column chromatography (CHCl$_3$/MeOH/H$_2$O 65/25/4), yielding 21.9 g (53% from 27) of a mixture of 29$\alpha$ and 29$\beta$.

EXAMPLE 13

Preparation of 5-O-|3'-(F-butyl)-2'-propenyl|-xylitol, 31

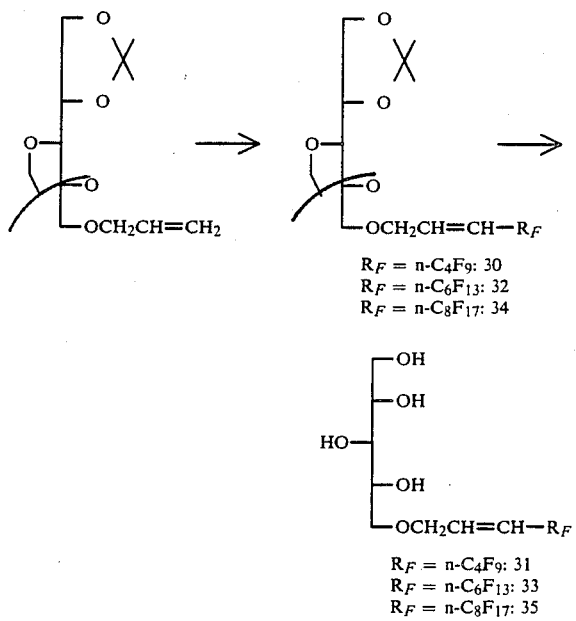

$R_F$ = n-C$_4$F$_9$: 30
$R_F$ = n-C$_6$F$_{13}$: 32
$R_F$ = n-C$_8$F$_{17}$: 34

$R_F$ = n-C$_4$F$_9$: 31
$R_F$ = n-C$_6$F$_{13}$: 33
$R_F$ = n-C$_8$F$_{17}$: 35

Step 1: Preparation of 5-O-|3'-(F-butyl)-2'-propenyl|-1,2:3,4-di-O-isopropylidene-xylitol, 30

40.9 g (0.15 mole) of 5-O-(2'-propenyl)-1,2:3,4-di-O-isopropylidene-xylitol dissolved in 220 ml of t-butanol are allowed to react with 102.6 ml of F-butyl iodide, in the presence of 8.86 g of copper chloride and 79.9 ml of ethanolamine. After 60 h of reflux at 110° C., 300 ml of water are added, and the mixture is extracted 4 times with 250 ml of ether. The ether solution is washed to neutrality, then dried over Na$_2$SO$_4$; the ether is evaporated and the product distilled (b.p.=90°-2° C./0.005 mm Hg). Yield: 60.2 g (82%) of 30.

C: 44.31 (44.10); H: 4.91 (4.73); F: 34.92 (34.87).

IR (film): $\nu$(C=C)=1680 cm$^{-1}$.

$^1$H (TMS): $\delta$(CH=CH)=5.68-6.57 ppm.

$^{19}$F (CCl$_3$F): $\delta$(CF$_2$CH=CH cis)=-108.6 ppm; $\delta$(CF$_2$CH=CH trans)=-112.6 ppm ratio cis/trans: 10/90.

Step 2: Preparation of 5-O-|3'-(F-butyl)-2'-propenyl|-xylitol, 31

89 ml of a mixture of CF$_3$CO$_2$H/H$_2$O (9/1 v/v) are added to 25 g (51.1 mmol) of the intermediate 30. After 30 mn of stirring the mixture is evaporated to dryness. After chromatography (CHCl$_3$/MeOH 10/1.5), 17.1 g, (82%) of 5-O-|3'-(F-butyl)-2'-propenyl|-xylitol, 31 are obtained.

C: 34.88 (35.13); H: 3.74 (3.69); F: 41.67 (41.68).

IR (KBr): $\nu$(OH)=3380 cm$^{-1}$; $\nu$(C=C)=1675 cm$^{-1}$.

$^{19}$F (CCl$_3$F): $\delta$(CF$_2$CH=CH cis)=-107.8 ppm; $\delta$(CF$_2$CH=CH trans)=-111.7 ppm ratio cis/trans: 10/90.

EXAMPLE 14

Preparation of 5-O-|3'-(F-hexyl)-2'-propenyl|xylitol, 33

Step 1: Preparation of 5-O-|3'-(F-hexyl)-2'-propenyl|-1,2:3,4-di-O-isopropylidene-xylitol, 32

The procedure described for example 13 is repeated, allowing 10 g (36.6 mmol) of 5-O-(2'-propenyl)-1,2:3,4-di-O-isopropylidene-xylitol to react with 44 ml of F-hexyl iodide. After treatment, 18.8 g (87%) of intermediate 32 are obtained.

b.p.=113°-4° C./0.005 mm Hg.

C: 40.92 (40.69); H: 4.04 (3.93); F: 41.77 (41.83).

IR (film): $\nu$(C=C)=1673 cm$^{-1}$.

$^1$H (TMS): $\delta$(CH=CH)=5.67-6.50 ppm.

$^{19}$F (CCl$_3$F): $\delta$(CF$_2$CH=CH cis)=-108.5 ppm; $\delta$(CF$_2$CH=CH trans)=-112 ppm; ratio cis/trans: 13/87.

Step 2: Preparation of 5-O-|3'-(F-hexyl)-2'-propenyl|-xylitol, 33

By a procedure identical to step 2 of example 8, the processing of 14 g (23.7 mmol) of intermediate 32 yields 8.1 g (67%) of 5-O-|3'-(F-hexyl)-2'-propenyl|-xylitol, 33.

C: 32.20 (32.96); H: 3.06 (2.96); F: 47.42 (48.40).

IR (KBr): $\nu$(OH)=3350 cm$^{-1}$; $\nu$(C=C)=1665 cm$^{-1}$.

$^{19}$F (CCl$_3$F): $\delta$(CF$_2$CH=CH cis)=-107.4 ppm; $\delta$(CF$_2$CH=CH trans)=-111.1 ppm; ratio cis/trans: 13/87.

EXAMPLE 15

Preparation of 5-O-|3'-(F-octyl)-2'-propenyl|-xylitol, 35

Step 1: Preparation of 5-O-|3'-(F-octyl)-2'-propenyl|-1,2:3,4-di-O-isopropylidene-xylitol, 34

By a procedure analogous to that described for example 13, the reaction in step 1 of 17.6 g (64.7 mmol) of 5-O-(2'-propenyl)-1,2:3,4-di-O-isopropylidene-xylitol with 70.5 ml of F-octyl iodide leads, after treatment, to 39,5 g (88%) of the intermediate 34.

b.p.=117°-8° C./0.005 mm Hg.

C: 38.57 (38.27); H: 3.57 (3.37); F: 47.52 (46.78).

IR (film): $\nu$(C=C)=1697 cm$^{-1}$.

$^1$H (TMS): $\delta$(CH=CH)=5.68-6.57 ppm.

$^{19}$F (CCl$_3$F): $\delta$(CF$_2$CH=CH cis)=-108.4 ppm; $\delta$(CF$_2$CH=CH trans)=112.3 ppm ratio cis/trans: 14/86.

Step 2: Preparation of 5-O-|3'-(F-octyl)-2'-propenyl|-xylitol, 35

By a procedure identical to step 2 of example 13, the processing of 16.1 g (23.3 mmol) of intermediate 34 yields 12.1 g (85%) of 5-O-|3'-(F-octyl)-2'-propenyl|-xylitol 35.

C: 31.03 (31.49); H: 2.47 (2.48); F: 51.53 (52.92).

IR (KBr): $\nu$(OH)=3364 cm$^{-1}$; $\nu$(C=C)=1678 cm$^{-1}$.

$^{19}$F (CCl$_3$F): δ(CF$_2$CH=CH cis)= −108.4 ppm; δ(CF$_2$CH=CH trans)= −112.3 ppm ratio cis/trans: 6/94.

EXAMPLE 16

Preparation of 5-O-|3'-(F-octyl)-propanoyl|-xylitol, 37

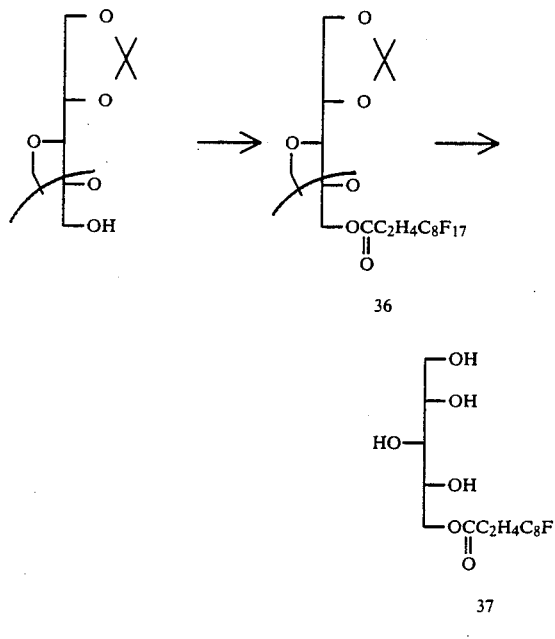

36

37

Step 1: Preparation of 5-O-|3'-(F-octyl)-propanoyl|-1,2:3,4-di-O-isopropylidene-xylitol, 36

To 2.8 g (12 mmol) of dry 1,2:3,4-di-O-isopropylidene-xylitol, dissolved in 50 ml of CHCl$_3$ and 1 ml of pyridine, are added dropwise 4.2 g (8.2 mmol) of 3-(F-octyl)-propanoyl chloride dissolved in 10 ml of anhydrous CHCl$_3$. After chromatography over silica (eluant CHCl$_3$/AcOEt 12/1) 5.55 g (95%) of 36 are obtained.

C: 37.39 (37.40); H: 3.39 (3.28); F: 46.07 (45.72).

IR (film): ν(C=O)=1747 cm$^{-1}$.

$^1$H (TMS): δ(CH$_3$)=1.42 ppm; 1.33 ppm ratio 3/1; δ(C$_2$H$_4$)=2.55-2.70 ppm.

$^{19}$F (CCl$_3$F): δ(CF$_2$CH$_2$)= −115 ppm.

$^{13}$C (TMS): δ(C=O)=171 ppm.

Step 2: Preparation of 5-O-|3'-(F-octyl)-propanoyl|-xylitol, 37

21.42 g (30 mmol) of 36, treated for 30 mn with 15 ml of a trifluoroacetic acid-water mixture (9/1 v/v), yield 11.67 g (62%) of 5-O-|3'-(F-octyl)-propanoyl|-xylitol, 37.

m.p.=111°-5° C.

C: 30.81 (30.68); H: 2.28 (2.41); F: 51.20 (51.57).

IR (KBr): ν(OH)=3460, 3300, 3210 cm$^{-1}$; ν(C=O)=1730 cm$^{-1}$.

$^1$H (TMS): δ(OH)=4.74 ppm; δ(CH$_2$OCO)=4.27 ppm (J=6.4 Hz).

$^{19}$F (CCl$_3$F): δ(CF$_2$CH$_2$)= −115 ppm.

$^{13}$C (TMS): δ(C=O)=173 ppm.

EXAMPLE 17

Preparation of 5-O-|11'-(F-hexyl)-undecanoyl|-xylitol, 39

In the same manner as example 16, the first step by reaction of 6 g (25.9 mmol) of 1,2:3,4-di-O-isopropylidene-xylitol with 11.6 g (22.2 mmol) of 11-(F-hexyl)-undecanoyl chloride gives, after treatment, 13 g (82%) of 38.

C: 46.28 (46.80); H: 5.40 (5.47); F: 34.42 (34.37).

IR (film): ν(C=O)=1740 cm$^{-1}$.

$^1$H (TMS): δ(CH$_3$)=1.37 ppm; 1.43 (12H).

$^{19}$F (CCl$_3$F): δ(CF$_2$CH$_2$)= −115 ppm.

$^{13}$C (TMS): δ(C=O)=173.7 ppm.

In step 2, 11.8 g (16.4 mmol) of 38 in contact with 32 ml of a trifluoroacetic acid-water mixture (9/1) yield 10 g (95%) of 5-O-|11'-(F-hexyl)-undecanoyl|-xylitol, 39. m.p.: 89°-90° C.

C: 41.57 (41.39); H: 5.05 (4.89); F: 38.38 (38.68).

IR (KBr): ν(OH)=3450 cm$^{-1}$, 3320 cm$^{-1}$; ν(C=O)=1730 cm$^{-1}$.

$^{19}$F (CCl$_3$F): δ(CF$_2$CH$_2$)= −113.6 ppm.

$^{13}$C (TMS): δ(C=O)=175.4 ppm; δ(CH$_2$CF$_2$)=31.6 ppm.

EXAMPLE 18

Preparation of 3,4-di-O-|3'-(F-octyl)-propanoyl|-D-mannitol, 41

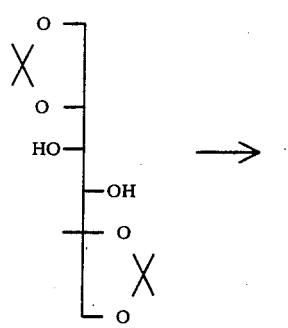

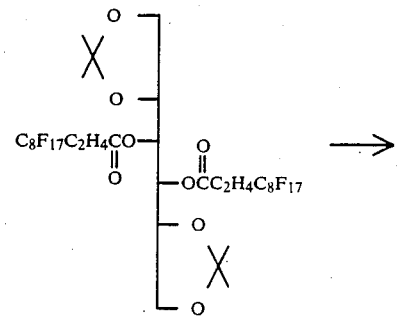

40

-continued

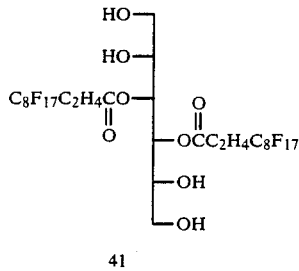

41

The same process as in example 16 applied to 4.70 g (17.9 mmol) of 1,2:5,6-di-O-isopropylidene-D-mannitol and 18.3 g (35.9 mmol) of 3-(F-octyl)-propanoyl chloride yields, after treatment and recrystallization from MeOH, 18.2 g (84%) of 3,4-di-O-|3'-(F-octyl)-propanoyl|-1,2:5,6-di-O-isopropylidene-D-mannitol, 40.

m.p.=93° C. $|\alpha|_D^{20}$=+8.6° (c 1 CHCl$_3$).
C: 33.47 (33.73); H: 2.26 (2.33); F: 55.61 (53.35).
IR (KBr): $\nu$(C=O)=1745 cm$^{-1}$.
$^1$H (TMS): $\delta$(CH$_3$)=1.37 ppm, 1.24 ppm; 1.24 ppm; $\delta$(H—C—OCO)=5.25 ppm.

In a second step the treatment of 0.5 g (0.4 mmol) of the intermediate product 40 dissolved in 4 ml of ethyl alcohol by a trifluoroacetic acid-water mixture (5/1 v/v) yields 0.32 g (70%) of 3,4-di-O-|3'-(F-octyl)-propanoyl|-D-mannitol, 41.
m.p.=135°-8° C.
IR (KBr): $\nu$(OH)=3310 cm$^{-1}$; $\nu$(C=O)=1720 cm$^{-1}$.

EXAMPLE 19
Preparation of
2-O-|3'-(F-octyl)-propanoyl|-1,4:3,6-dianhydro-D-mannitol, 42 the diester 43 are separated with preparative HPLC (eluant CHCl$_3$/CH$_3$CN 10/2), yielding 8.12 g (43%) of monoester 42 and 7.83 g (24%) of diester 43.
The monoester 42 is recrystallized from hexane:
m.p.=93° C. $|\alpha|_D^{24}$=+48.4° (c 1 CHCl$_3$).
C: 33.00 (32.91); H: 1.95 (2.11); F: 51.84 (52.07).
IR (KBr): $\nu$(OH)=3490 cm$^{-1}$; $\nu$(C=O)=1745 cm$^{-1}$.
$^{19}$F (CCl$_3$F): $\delta$(CF$_2$CH$_2$)=−115 ppm.
$^{13}$C (TMS): $\delta$(C=O)=170.9 ppm; $\delta$(C-2)=74.9 ppm; $\delta$(C-5)=72.4 ppm.
The diester 43 is recrystallized from hexane:
m.p.=108° C. $|\alpha|_D^{20}$=+52° (c 1 CHCl$_3$).
C: 30.74 (30.73); H: 1.31 (1.47); F: 59.60 (59.02).
IR (KBr): $\nu$(C=O)=1745 cm$^{-1}$.
$^{19}$F (CCl$_3$F): $\delta$(CF$_2$CH$_2$)=−115 ppm.
$^{13}$C (TMS): $\delta$(C=O)=170.9 ppm (2c); $\delta$(C-2, C-5)=74.5 ppm.

EXAMPLE 20
Preparation of
2-O-|3'-(F-pentyl)-propanoyl|-1,4:3,6-dianhydro-D-mannitol, 44

A process comparable to that described in example 19 when applied to 4.51 g (30.9 mmol) of isomannide and 4.26 g (11.8 mmol) of 3-(F-pentyl)-propanoyl chloride gives, after treatment, 3.99 g (72%) of monoester 44:
m.p.=41°-2° C.; $|\alpha|_D^{25}$=+63.3° (c 1 CHCl$_3$).
IR (KBr): $\delta$(OH)=3466 cm$^{-1}$; $\delta$(C=O)=1745 cm$^{-1}$.
$^{13}$C (TMS): $\delta$(C=O)=170.8 ppm; $\delta$(C-2)=74.8 ppm; $\delta$(C-5)=72.3 ppm.
and 0.67 g (7%) of diester 45:
m.p.=29°-30° C.; $|\alpha|_D^{25}$=+67.1° (c 1.2 CHCl$_3$).
IR (film): $\delta$(C=O)=1740 cm$^{-1}$.
$^{13}$C (TMS): $\delta$(C=O)=170.9 ppm (2c); $\delta$(C-2, C-5)=74.5 ppm.

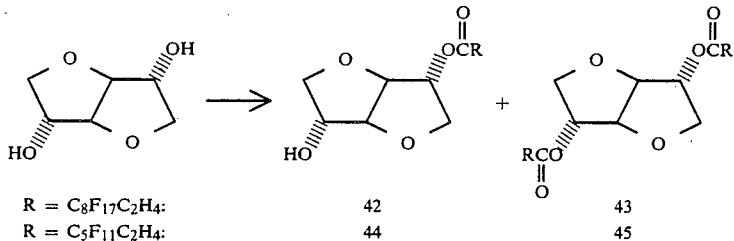

R = C$_8$F$_{17}$C$_2$H$_4$:   42    43
R = C$_5$F$_{11}$C$_2$H$_4$:  44    45

To 5.28 g (36 mmol) of isomannide in 200 ml of anhydrous CHCl$_3$ and 4 ml of anhydrous pyridine are added 15.39 g (30 mmol) of 3-(F-octyl)-propanoyl chloride; the mixture is stirred for 24 h at room temperature. After evaporation of the CHCl$_3$, the crude reaction product is dissolved with ether, washed with water, then with an aqueous solution of 1.4M HCl, then with water. After drying over Na$_2$SO$_4$, the monoester 42 and

EXAMPLE 21
2-O-|3'-(F-octyl)-propanoyl|-1,4:3,6-dianhydro-D-sorbitol, 46, 5-O-|3'-(F-octyl)-propanoyl|-1,4:3,6 dianhydro-D-sorbitol, 47 and
2,5-di-O-|3'-(F-octyl)-propanoyl|-1,4:3,6 dianhydro-D-sorbitol, 48

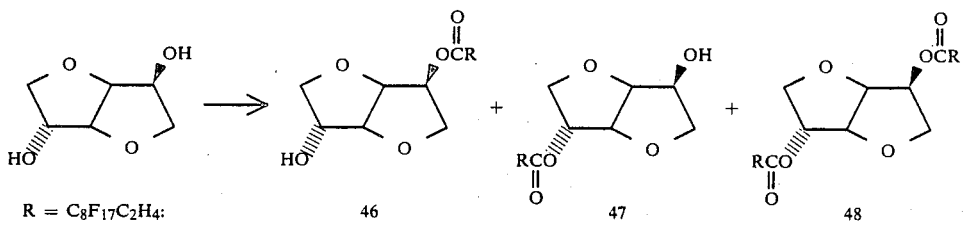

R = C$_8$F$_{17}$C$_2$H$_4$:    46    47    48

12.32 g (24.1 mmol) of 3-(F-octyl)-propanoyl chloride are added to 9 g (60 mmol) of isosorbide dissolved in 340 ml of CHCl$_3$ and 2.7 ml of anhydrous pyridine. After stirring for 72 h, the solution is evaporated and the residue redissolved in a minimum of water and ether. The solid that precipitates is filtered, yielding 4.23 g of substrate 46 which is purified by recrystallization from a hexane/methanol mixture. The ether phase of the filtrate is washed to neutrality and dried; after evaporation, a mixture of the monoesters 46 and 47, and of the diester 48 (9.46 g) is obtained, and is separated by chromatography over silica (eluant CHCl$_3$/MeOH:10/0.5).

A total of 7.94 g (53%) of the monoester 46 is obtained:
m.p.=113°–118° C. $|\alpha|_D^{21}$=+20.6° (c 1 acetone).
$^1$H (TMS): δ(OH)=3.55 ppm.
$^{19}$F (CCl$_3$F): δ(CF$_2$CH$_2$)= −114 ppm.
ms (IE): peak at m/e=128 (65%), loss of R$_F$C$_2$H$_4$CO$_2$.

2.96 g (20%) of monoester 47:
m.p.=107°–111° C. $|\alpha|_D^{21}$=+34.6° (c 1 acetone).
$^1$H (TMS): δ(OH)=4.23 ppm.
$^{19}$F (CCl$_3$F): δ(CF$_2$CH$_2$)= −114 ppm.
ms (IE): peak at m/e=128 (99%), loss of R$_F$C$_2$H$_4$CO$_2$.

and 1.2 g (4.5%) of the diester 48:
m.p.=115°–8° C.

EXAMPLE 22

6-O-|3′-(F-octyl)-propanoyl|-1,4-D-sorbitan,

R = C$_8$F$_{17}$CH$_2$CH$_2$:  49
R = C$_8$F$_{17}$(CH$_2$)$_{10}$  50

A solution of 9.22 g (18 mmol) of 3-(F-octyl)-propanoyl chloride in anhydrous chloroform is added dropwise to 5.89 g (35.9 mmol) of 1,4-D-sorbitan in 22 ml of anhydrous pyridine. After 24 h at room temperature, the precipitate is filtered, washed with water then with CHCl$_3$, yielding, after crystallization from MeOH, 6.85 g (60%) of 49.

m.p.=134°–6° C. $|\alpha|_D^{18}$= −2° (c 1 DMSO).
C: 32.04 (31.99); H: 2.39 (2.37); F: 50.62 (50.60).
IR: ν(OH)=3440 cm$^{-1}$; ν(C=O)=1720 cm$^{-1}$.
$^{13}$C (TMS): δ(C=O)=172 ppm; δ($\underline{C}$H$_2$OCO)=69.1 ppm.
ms (CI: NH$_3$): M+638 (34%).

EXAMPLE 23

Preparation of
6-O-|11′-(F-octyl)-undecanoyl|-1,4-D-sorbitan, 50

A process similar to that used in example 22, applied to 2.6 g (15.8 mmol) of 1,4-anhydro-D-sorbitol and 3.3 g (5.3 mmol) of 11-(F-octyl)-undecanoyl chloride, gives, after treatment and recrystallisation from MeOH, 2.5 g (67%) of 50.

m.p.=126° C. $|\alpha|_D^{26}$= −1° (c 1.1 DMSO).
C: 40.71 (40.01); H: 4.22 (4.16); F: 42.86 (43.03).
IR (KBr): ν(OH)=3395 cm$^{-1}$; ν(C=O)=1730 cm$^{-1}$.
$^{13}$C (TMS): δ(C=O)=175.8 ppm; δ($\underline{C}$H$_2$OCO)=69 ppm.

EXAMPLE 24

|3′-(F-octyl)-propanoyl|-N-methyl-D-glucamide, 51

To 5.12 g (10.4 mmol) of 3-(F-octyl)-propanoic acid in 20 ml of anhydrous diethyl ether cooled to 0° C. under dry argon, one adds 1 ml (13.2 mmol) of anhydrous pyridine, then 1.36 g (12.5 mmol) of ethyl chloroformiate. The activated perfluoroalkylated acid is added after filtration to 2.03 g (10.4 mmol) of N-methyl-D-glucamine in 25 ml of anhydrous MeOH at 50° C. After 1$^h$30 at 50° C. and a night at 0° C. the mixture is filtered. The precipitate is recrystallized from MeOH; 3.23 g (60%) of 51 are obtained. After chromatography over silica (eluant CHCl$_3$/MeOH 1/1) and recrystallization in methanol or dioxane, 2.23 g (32%) of |3′-(F-octyl)-propanoyl|-N-methyl-D-glucamide 51 are obtained.

m.p.=79°–81° C. $|\alpha|_D^{20}$= −8.0° (c 1.2 DMSO).
C: 32.17 (32.30); H: 3.09 (3.01); F: 48.18 (48.25).
IR (KBr): ν(OH)=3360 cm$^{-1}$; ν(C=O)=1630 cm$^{-1}$.
$^1$H (TMS): δ(NCH$_3$)=2.95 ppm.
$^{19}$F (CCl$_3$F): δ(CF$_2$CH$_2$)= −113 ppm.

In analogous manner, the following compounds, which are encompassed by the present invention, have been prepared:

3′-(F-hexyl)-propyl-β-D-xylopyranoside; 3′-(F-hexyl)-propyl-β-L-rhamnopyranoside;

2′-(F-butyl)-ethyl-4-O-(α-D-glucopyranosyl)-β-D-glucopyranoside or

2′-(F-butyl)-ethyl-β-D-maltopyranoside;

3′-(F-butyl)-propyl-4-O-(α-D-glucopyranosyl)-β-D-glucopyranoside or

3′-(F-butyl)-propyl-β-D-maltopyranoside;

3′-(F-hexyl)-propyl-4-O-(α-D-glucopyranosyl)-β-D-glucopyranoside or

3′-(F-hexyl)-propyl-β-D-maltopyranoside;

3′-(F-octyl)-propyl-4-O-(α-D-glucopyranosyl)-β-D-glucopyranoside or

3′-(F-octyl)-propyl-β-D-maltopyranoside;

11'-(F-butyl)-undecyl-4-O-(α-D-glucopyranosyl)-β-D-glucopyranoside or
11'-(F-butyl)-undecyl-β-D-maltopyranoside;
11'-(F-hexyl)-undecyl-4-O-(α-D-glucopyranosyl)-β-D-glucopyranoside or
11'-(F-hexyl)-undecyl-β-D-maltopyranoside;
11'-(F-octyl)-undecyl-4-O-(α-D-glucopyranosyl)-β-D-glucopyranoside or
11'-(F-octyl)-undecyl-β-D-maltopyranoside;
2'-(F-hexyl)-ethyl-4-O-(β-D-galactopyranosyl)-β-D-glucopyranoside or
2'-(F-hexyl)-ethyl-β-D-lactopyranoside;
2'-(F-octyl)-ethyl-4-O-(β-D-galactopyranosyl)-β-D-glucopyranoside or
2'-(F-octyl)-ethyl-β-D-lactopyranoside;
2'-(F-octyl)-ethyl-4-O-(β-D-glucopyranosyl)-β-D-glucopyranoside or
2'-(F-octyl)-ethyl-β-D-cellobiopyranoside; 6-O-|3'-(F-butyl)-2'-propenyl|-D-galactose;
6-O-|3'-(F-octyl)-2'-propenyl|-D-galactose; 3-O-|3'-(F-butyl)-2'-propenyl|-D-glucose;
3-O-|3'-(F-hexyl)-2'-propenyl|-D-glucose; 3-O-|3'-(F-octyl)-2'-propenyl|-D-glucose;
6-O-|3'-(F-butyl)-propyl|-D-galactose; 6-O-|3'-(F-octyl)-propyl|-D-galactose;
3-O-|3'-(F-butyl)-propyl|-D-glucose; 3-O-|3'-(F-hexyl)-propyl|-D-glucose;
3-O-|3'-(F-octyl)-propyl|-D-glucose; 3-O-|3'-(F-pentyl)-propanoyl|-D-glucose;
3-O-|3'-(F-heptyl)-propanoyl|-D-glucose; 6-O-|3'-(F-pentyl)-propanoyl|-D-galactose;
6-O-|3'-(F-heptyl)-propanoyl|-D-galactose;
6-O-|11'-(F-octyl)-undecanoyl|-D-galactose; 3-O-|3'-(F-octyl)-propanoyl|-D-xylose;
6-O-|3'-(F-octyl)-propanoyl|-D-fructose; 1-O-|3'-(F-octyl)-propanoyl|-D-fructose;
β-D-fructofuranosyl-6-O-|3'-(F-octyl)-propanoyl|-α-D-glucopyranoside or
6-O-|3'-(F-octyl)-propanoyl|-sucrose;
6-O-|3'-(F-octyl)-propanoyl|-β-D-fructopyranosyl 6-O-|3'-(F-octyl)-propanoyl|-α-D-glucopyranoside or
6,6'-di-|3'-(F-octyl)-propanoyl|-sucrose;
5-O-|3'-(F-butyl)-propyl|-xylitol;
5-O-|3'-(F-pentyl)-propanoyl|-xylitol; 5-O-|3'-(F-heptyl)-propanoyl|-xylitol;
5-O-|11'-(F-hexyl)-undecanoyl|-xylitol;
|3'-(F-pentyl)-propanoyl|-N-methyl-D-glucamide;
|3'-(F-heptyl)-propanoyl|-N-methyl-D-glucamide;
2-deoxy-2-|3'-(F-octyl)-propanamido|-D-glucose;
2-deoxy-2-|3'-(F-octyl)-propanamido|-D-glucitol; and
3-O-|3'-(F-octyl)-propanoyl|-myo-inositol.

SURFACTANT ACTIVITY

The strong surface activity of the compounds encompassed by this invention is illustrated in particular by the strong lowering of the surface tension ($\gamma_s$) they cause when added to water, as shown by the examples of surface tensions, measured at 20° C. and expressed in milliNewton.meter$^{-1}$, (mNm$^{-1}$), collected in the Table below:

| Compound | Concentration in water | $\gamma_s$(mNm$^{-1}$) (±0.3) | $\gamma_i$(mNm$^{-1}$) (±0.3) |
|---|---|---|---|
| 2'-(F-hexyl)-ethyl-D-maltopyranoside, 26 | 0.1% | 25.2 | 4.7 |
| 2'-(F-octyl)-ethyl-D-maltopyranoside, 29 | 0.1% | 22.3 | 2.6 |
| 5-O-|3'-(F-butyl)-2'-propenyl|-xylitol, 31 | 0.1% | 19.7 | 2.4 |
| 5-O-|3'-(F-hexyl)-2'-propenyl|-xylitol, 33 | 0.01% | 17.8 | 1.0 |
| 6-O-|3'-(F-butyl-2'-propenyl|-D-galactose, | 0.05% | 20.2 | 1.4 |
| 6-O-|3'-(F-hexyl-2'-propenyl|-D-galactose, 15 | 0.01% | 20.9 | 1.4 |

More specifically, the action of these compounds at the interface between water and the fluorocarbons is demonstrated by the very sharp diminution of the interfacial tension ($\gamma_i$) between water and perfluorodecalin (56 mNm$^{-1}$ in the absence of surfactant), as illustrated by the examples collected in the same Table.

The co-surfactant character of the compounds concerned by the invention is illustrated in particular by the sharp diminution of the surface tension ($\gamma_s$) they provoke when added to a solution in water of 1 g/l of Pluronic F-68 (a commercial surfactant used in the preparation of emulsions of fluorocarbons for biomedical use, such as Fluosol-DA or Oxypherol) from $\gamma_s = 47 \pm 0.3$ mNm$^{-1}$ to the values collected for a few examples in the Table below:

| Compound | Dispersion in 1 g/l of Pluronic F-68 in water (% with respect to Pluronic F-68) | $\gamma_s$(mNm$^{-1}$) (±0.3) | $\gamma_i$(mNm$^{-1}$) (±0.3) |
|---|---|---|---|
| 3-O-|3'-(F-octyl)-propanoyl|-D-glucose, 8 | 10 mg/l (1%) | 20.2 | 4.1 |
| 5-O-|3'-(F-octyl)-2'-propenyl|-xylitol, 35 | 10 mg/l (1%) | 19.5 | 2.8 |
| 5-O-|3'-(F-octyl)-propanoyl|-xylitol, 37 | 200 mg/l (20%) | 23.7 | 4.3 |

More specifically, the action of these compounds on the interface between water and fluorocarbons is demonstrated by the very sharp diminution of the interfacial tension ($\gamma_i$) between dispersions of these compounds in a solution of Pluronic F-68 at 1 g/l in water and perfluorodecalin. The interfacial tension is thus lowered from $\gamma_i = 31$ mNm$^{-1}$ with Pluronic F-68 alone, to the values collected in the same Table.

The stabilisation effect which can be obtained on the emulsions by incorporating the new surfactants is illustrated, for example, by the fact that the increase in particle size is 6 times less after 30 days at 50° C. for a 20% weight/volume emulsion of F-decalin prepared with 2% (w/v) of Pluronic F-68 and 1% (w/v) of 5-O-|3'-(F-octyl)-2'-propenyl|-xylitol, 35, as surfactants, than for a reference emulsion prepared similarly but with 3% of Pluronic F-68 as the sole surfactant. It is also noteworthy that the particle size is still smaller in the fluorinated surfactant-containing emulsion maintained at 50° C. for 30 days than for the reference emulsion stored at 4° C. for the same length of time.

The biocompatibility of compounds belonging to the present invention is illustrated, in particular, by the fact that aqueous solutions of these compounds, and dispersions of these compounds in aqueous solutions of Pluronic F-68, for example: a solution of 0.1 g/l of 2'-(F-hexyl)-ethyl-D-glucopyranoside, 3, a solution of 0.1 g/l of |3'-(F-octyl)-propanoyl|-N-methyl-D-glucamide, 51, a solution of 0.1 g/l of 6-O-|3'-(F-butyl)-2'-propenyl|-D-galactose, or a dispersion of 1 g of 2'-(F-octyl)ethyl-D-maltopyranoside, 29, in a solution, of 1 g/l of Pluronic F-68 in water, all these solutions and dispersions containing 9% o of NaCl, do not perturb the growth and multiplication of lymphoblastoid cell cultures of the Namalva strain.

Likewise, the biocompatibility of compounds belonging to the invention is illustrated by the fact that aqueous solutions of 100 g/l of 2'-(F-hexyl)-ethyl-D-maltopyranoside, 26, or of 1 g/l of 6-O-|3'-(F-butyl)-2'-propenyl|D-galactose, or a dispersion of 1 g/l of 2'-(F-octyl)ethyl-D-maltopyranoside, 29, in a solution of 1 g/l of Pluronic F-68 in water, or a dispersion of 16 g/l of 6-O-|3'-(F-hexyl)-2'-propenyl|-D-galactose, 33, in a solution of 1 g/l of Pluronic F-68 in water, or a dispersion of 20 g/l of 5-O-|3'-(F-octyl)-2'-propenyl|-xylitol, 35, in a solution of 10 g/l of Pluronic F-68 in water, all these solutions and dispersions containing 9% o of NaCl, do not cause the hemolysis of human red blood cells.

In the same way the biocompatibility of such compounds is illustrated by the fact that a solution, in water containing 9% o of NaCl, of 10 g/l of 2'-(F-hexyl)-ethyl-D-maltopyranoside, 26, or dispersions in a solution at 10 g/l of Pluronic F-68 in water containing 9% o of NaCl, of 20 g/l of 5-O-|3'-(F-octyl)-2'-propenyl|-xylitol, 35, or of 20 g/l of 6-O-|3'-(F-butyl)-2'-propenyl|-D-galactose, or of 20 g/l of 6-O-|3'-F-hexyl)-2'-propenyl|-D-galactose, 15, or of 20 g/l of 5-O-|3'-(F-butyl)-2'-propenyl|-xylitol, 31, when injected in quantities of 500 μl into 10 mice of 20–25 g, caused no deaths, and did not perturb the normal growth of the animals, which were observed for 35 days.

The biocompatibility of the above compounds is moreover illustrated by the fact that an emulsion of bis-(F-butyl)-ethene at 10% by weight, obtained by dilution of a stem emulsion containing 20% of the fluorocarbon by weight prepared from a dispersion of 10 g/l of 5-O-|3'-(F-octyl)-2'-propenyl|-xylitol, 35, in a solution of 20 g/l of Pluronic F-68, was perfused successfully into rats until a hematocrit of 15 volumes % was reached.

EXAMPLE OF COMPOSITION

An emulsion having the following composition was prepared:

| INGREDIENTS | | PROPORTIONS (weight/volume) |
|---|---|---|
| Compound of Example 15 | | 1% |
| Pluronic F68 | | 2% |
| Bis(F-butyl)-1,2-ethene | | 20% |
| Water | q.s.p. | 100% |

The surfactants are added to water. Then the bis(F-butyl)ethene is added under agitation in a homogenizer. The obtained emulsion may be used as oxygen carrier.

In the preceding composition, the compound of Example 12 may be substituted to the compound of Example 15 and bis(F-hexyl)-1,2-ethene may be substituted to the bis(F-butyl)ethene.

We claim:

1. Compounds having a polyhydroxylated hydrophilic moiety, a highly fluorinated moiety and a functional junction group linking said moieties together, wherein said hydrophilic moiety is derived from a sugar which is a monoholoside or diholoside, a polyol containing at least 4 hydroxyl groups, or an aminopolyol having at least 3 hydroxyl groups, and wherein said highly fluorinated moiety consists of a fluorocarbon group wherein at least 50% of the atoms bonded to the carbon skeleton are fluorine atoms, the other atoms bonded to the carbon skeleton being hydrogen, chlorine or bromine atoms, said highly fluorinated moiety containing at least 4 fluorine atoms as well as the internal ethers and ketals thereof, said compounds having a discrete molecular weight.

2. A compound according to claim 1 wherein said functional junction group links said hydrophilic and fluorinated moieties through an ether, ester, amide or amine group.

3. A compound according to claim 1, wherein the highly fluorinated moiety is present in the form of a $R_F$-W-group wherein $R_F$ is selected from the group consisting of:

| | |
|---|---|
| $F(CF_2)_v$- | with $2 \leq v \leq 12$ |
| $(CF_3)_2CF(CF_2)_w$- | $0 \leq w \leq 8$ |
| $R_{F1}[CF_2CF(CF_3)]_r$- | $1 \leq r \leq 4$ |

$R_{F1}$ being $CF_3-$, $C_2F_5-$ or $(CF_3)_2CF-$,

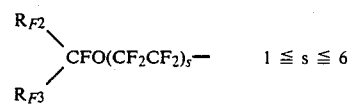
$1 \leq s \leq 6$ $R_{F2}$ and $R_{F3}$, identical or different, being selected from $CF_3-$, $C_2F_5-$, $n-C_3F_7$ or $CF_3CF_2CF(CF_3)-$,
or $R_{F2}$ and $R_{F3}$ representing together $-(CF_2)_4-$ or $-(CF_2)_5-$,

| | |
|---|---|
| $CF_3CF_2O(CF_2CF_2O)_tCF_2-$ | $0 \leq t \leq 6$ |
| and $CF_3(CF_2)_2O[CF(CF_3CF_2O]_uCF(CF_3)-$ | $0 \leq u \leq 6$ | and W is selected from the group consisting of:
—$(CH_2)_n$—
—$(CH_2)_p$CH=CH—$(CH_2)_q$—
—$(CH_2)_m$—CO—
—$(CH_2)_j$OCH$_2$CH(OH)CH$_2$— and
—$(CH_2)_k$OCH$_2$CH(CH$_2$OH)—
(wherein in the last three cases $R_F$ is bonded to the carbon atom of the left end of the W group),
wherein
n may vary from 1 to 12,
m may vary from 0 to 12,
the sum (p+q) may vary from 1 to 12,
j and k may vary from 1 to 12, it being understood that W can still contain a —(CH₂C-H₂O)y— polyoxyethylene, a —CH(CH₃)CH₂O y— polyoxypropylene or a —(CH₂CH₂S)y— polythioethylene segment, or a mixture of such segments, with 1≦y≦12, and that in the R_F— chain, part of the fluorine atoms can be replaced by H, Cl or Br atoms, in a proportion such that at least 50% of the atoms bonded to the carbon skeleton of R_F— are fluorine atoms, with at least 4 fluorine atoms being present in said chain.

4. A compound according to claim 1, having the formula I

wherein:
X represents —CH=O, —CH₂OR₄, —CH₂N(R₅)R₆ or —CH(OR₇)—,
Y represents —CH(OR₈)—, —CO— or —CH(NR₅R₆)—,
Z represents —H, —CH₃, —CH₂OR₉ or —CH(OR₁₀)—,
it being understood that:
when X is —CH=O, then Y represents —CH(OR₈)— or —CH(NR₅R₆)—,
when X is —CH₂N(R₅)R₆, then Y represents —CH(OR₈)—,
when Z is —CH(OR₁₀)—, then X represents —CH(OR₇)— and then the divalent groups X and Z are linked together through a covalent bond,
and when Y is —CH(NR₅R₆)—, then X represents —CH=O or —CH₂OR₄,
and the R₁ to R₁₀ groups, which may be identical or different, are selected from —H, C₁-C₁₈ alkyl, C₂-C₁₈ unsaturated alkyl, a deoxy-oside group, a —(CH₂C-H₂O)y—H, —[CH(CH₃)CH₂O]y—H or (CH₂CH₂S)y—H group, or a mixture of said groups, wherein 1≦y≦12, and a highly fluorinated group as defined below.
with the proviso that at least one of the R₁ through R₁₀ groups represents a group having a highly fluorinated substituent; as well as internal ethers and ketals thereof.

5. A compound according to claim 1, selected from the group consisting of
the 2'-(F-hexyl)-ethyl-β-D-glucopyranoside,
the 2'-(F-hexyl)-ethyl-α-D-glucopyranoside,
the 2'-(F-octyl)-ethyl-β-D-glucopyranoside,
the 2'-(F-octyl)-ethyl-α-D-glucopyranoside,
the 2'-(F-hexyl)-ethyl-β-D-galactopyranoside,
the 2'-(F-hexyl)-ethyl-α-D-galactopyranoside,
the 3'-(F-hexyl)-propyl-β-D-xylopyranoside,
the 3'-(F-hexyl)-propyl-β-L-rhamnopyranoside,
the 2'-(F-butyl)-ethyl-4-O-(α-D-glucopyranosyl)-β-D-glucopyranoside, or 2'-(F-butyl)-ethyl-β-D-maltopyranoside,
the 2'-(F-hexyl)-ethyl-4-O-(α-D-glucopyranosyl)-β-D-glucopyranoside, or 2'-(F-hexyl)-ethyl-β-D-maltopyranoside,
the 2'-(F-hexyl)-ethyl-4-O-(α-D-glucopyranosyl)-α-D-glucopyranoside, or 2'-(F-hexyl)-ethyl-α-D-maltopyranoside,
the 2'-(F-octyl)-ethyl-4-O-(α-D-glucopyranosyl)-β-D-glucopyranoside, or 2'-(F-octyl)-ethyl-β-D-maltopyranoside,
the 2'-(F-octyl)-ethyl-4-O-(α-D-glucopyranosyl)-α-D-glucopyranoside, or 2'-(F-octyl)-ethyl-α-D-maltopyranoside,
the 3'-(F-butyl)-propyl-4-O-(α-D-glucopyranosyl)-β-D-glucopyranoside or 3'-(F-butyl)-propyl-β-D-maltopyranoside,
the 3'-(F-hexyl)-propyl-4-O-(α-D-glucopyranosyl)-β-D-glucopyranoside or 3'-(F-hexyl)-propyl-β-D-maltopyranoside,
the 3'-(F-octyl)-propyl-4-O-(α-D-glucopyranosyl)-β-D-glucopyranoside or 3'-(F-octyl)-propyl-β-D-maltopyranoside,
the 11'-(F-butyl)-undecyl-4-O-(α-D-glucopyranosyl)-β-D-glucopyranoside or 11'-(F-butyl)-undecyl-β-D-maltopyranoside,
the 11'-(F-hexyl)-undecyl-4-O-(α-D-glucopyranosyl)-β-D-glucopyranoside or 11'-(F-hexyl)-undecyl-β-D-maltopyranoside,
the 11'-(F-octyl)-undecyl-4-O-(α-D-glucopyranosyl)-β-D-glucopyranoside or 11'-(F-octyl)-undecyl-β-D-maltopyranoside,
the 2'-(F-hexyl)-ethyl-4-O-(β-D-galactopyranosyl)-β-D-glucopyranoside or 2'-(F-hexyl)-ethyl-β-D-lactopyranoside,
the 2'-(F-octyl)-ethyl-4-O-(β-D-galactopyranosyl)-β-D-glucopyranoside or 2'-(F-octyl)-ethyl-β-D-lactopyranoside,
the 2'-(F-octyl)-ethyl-4-O-(β-D-glucopyranosyl)-β-D-glucopyranoside or 2'-(F-octyl)-ethyl-β-D-cellobiopyranoside,
the 6-O-|3'-(F-butyl)-2'-propenyl|-D-galactose,
the 6-O-|3'-(F-hexyl)-2'-propenyl|-D-galactose,
the 6-O-|3'-(F-octyl)-2'-propenyl|-D-galactose,
the 3-O-|3'-(F-butyl)-2'-propenyl|-D-glucose,
the 3-O-|3'-(F-hexyl)-2'-propenyl|-D-glucose,
the 3-O-|3'-(F-octyl)-2'-propenyl|-D-glucose,
the 6-O-|3'-(F-butyl)-propyl|-D-galactose,
the 6-O-|3'-(F-hexyl)-propyl|-D-galactose,
the 6-O-|3'-(F-octyl)-propyl|-D-galactose,
the 3-O-|3'-(F-butyl)-propyl|-D-glucose,
the 3-O-|3'-(F-hexyl)-propyl|-D-glucose,
the 3-O-|3'-(F-octyl)-propyl|-D-glucose,
the 3-O-|3'-(F-pentyl)-propanoyl|-D-glucose,
the 3-O-|3'-(F-heptyl)-propanoyl|-D-glucose,
the 3-O-|3'-(F-octyl)-propanoyl|-D-glucose,
the 6-O-|3'-(F-pentyl)-propanoyl|-D-galactose,
the 6-O-|3'-(F-heptyl)-propanoyl|-D-galactose,
the 6-O-|3'-(F-octyl)-propanoyl|-D-galactose,
the 3-O-|11'-(F-hexyl)-undecanoyl|-D-glucose,
the 6-O-|11'-(F-butyl)-undecanoyl|-D-galactose,
the 6-O-|11'-(F-hexyl)-undecanoyl|-D-galactose,
the 6-O-|11'-(F-octyl)-undecanoyl|-D-galactose,
the 3-O-|3'-(F-octyl)-propanoyl|-D-xylose,
the 6-O-|3'-(F-octyl)-propanoyl|-D-fructose,
the 1-O-|3'-(F-octyl)-propanoyl|-D-fructose,
the β-D-fructofuranosyl-6-O-|3'-(F-octyl)-propanoyl|-α-D-glucopyranoside or 6-O-|3'-(F-octyl)-propanoyl|-sucrose,
the 6-O-|3'-(F-octyl)-propanoyl|-β-D-fructopyranosyl 6-O-|3'-(F-octyl)-propanoyl|-α-D-glucopyranoside, or 6,6'-di-|3'-(F-octyl)-propanoyl|-sucrose,
the 5-O-|3'-(F-butyl)-2'-propenyl|-xylitol,
the 5-O-|3'-(F-hexyl)-2'-propenyl|-xylitol,
the 5-O-|3'-(F-octyl)-2'-propenyl|-xylitol,
the 5-O-|3'-(F-butyl)-propyl|-xylitol,
the 5-O-|3'-(F-pentyl)-propanoyl|-xylitol,
the 5-O-|3'-(F-heptyl)-propanoyl|-xylitol,
the 5-O-|3'-(F-octyl)-propanoyl|-xylitol,
the 5-O-|11'-(F-hexyl)-undecanoyl|-xylitol,
the 3,4-di-O-|3'-(F-octyl)-propanoyl|-D-mannitol, the 2-O-|3'-(F-pentyl)-propanoyl|-1,4:3,6-dianhydro-D-mannitol,
the 2-O-|3'-(F-octyl)-propanoyl|-1,4:3,6-dianhydro-D-mannitol,
the 2-O-|3'-(F-octyl)-propanoyl|-1,4:3,6-dianhydro-D-sorbitol,
the 5-O-|3'-(F-octyl)-propanoyl|-1,4:3,6-dianhydro-D-sorbitol,
the 6-O-|3'-(F-octyl)-propanoyl|-1,4-D-sorbitan,
the 6-O-|11'-(F-octyl)-undecanoyl|-1,4-D-sorbitan,
the |3'-(F-pentyl)-propanoyl|-N-methyl-D-glucamide,
the |3'-(F-heptyl)-propanoyl|-N-methyl-D-glucamide,
the |3'-(F-octyl)-propanoyl|-N-methyl-D-glucamide
the 2-deoxy-2-|3'-(F-octyl)-propanamido|-D-glucose,
the 2-deoxy-2-|3'-(F-octyl)-propanamido|-D-glucitol, and
the 3-O-|3'-(F-octyl)-propanoyl|-myo-inositol.

6. A process for the preparation of the compounds of claim 1, characterized by the fact that the starting material is said polyol or aminopolyol, or a derivative thereof, including internal ethers or ketals thereof, wherein the hydroxyl groups, or part thereof, are protected, or wherein at least one hydroxyl group is replaced by a leaving group, that said starting material is reacted with a highly fluorinated derivative so as to link the polyol or aminopolyol moiety with the highly fluorinated moiety through a functional junction group, and that the protected groups, when present, are deprotected.

7. A process according to claim 6, wherein the hydrophilic starting material is reacted with a member of the group consisting of:
(a) an alcohol $R_F$—W—OH, where $R_F$—W— is other than acyl,
(b) an amine $R_F$—W—NH(R''), where $R_F$—W— is other than acyl, P'' being —H, $C_1$-$C_{18}$ alkyl, $C_2$-$C_{18}$ unsaturated alkyl or $R_F$—W— and where the hydrophilic starting material has a leaving group,
(c) a mixed anhydride $R_F$—W—O—CO—OAlk, Alk being lower alkyl, or an acyl chloride $R_F$—W—Cl where $R_F$ is an acyl and where the starting material is an aminopolyol, and
(d) an acylchloride $R_F$—W—Cl, where $R_F$—W— is acyl,
wherein $R_F$—W comprises a group wherein $R_F$ is selected from the group consisting of:

| | |
|---|---|
| $F(CF_2)_v$- | with $2 \leq v \leq 12$ |
| $(CF_3)_2CF(CF_2)_w$- | $0 \leq w \leq 8$ |
| $R_F1[CF_2CF(CF_3)]_r$- | $1 \leq r \leq 4$ |

$R_F1$ being $CF_3$—, $C_2F_5$— or $(CF_3)_2CF$—,

| | | |
|---|---|---|
| $R_F2$ $R_F3$ | $CFO(CF_2CF_2)_s$- | $1 \leq s \leq 6$ |

$R_F2$ and $R_F3$, identical or different, being selected from $CF_3$—, $C_2F_5$—, n—$C_3F_7$ or $CF_3CF_2CF(CF_3)$—, or $R_F2$ and $R_F3$ representing together —$(CF_2)_4$— or —$(CF_2)_5$—,

| | |
|---|---|
| $CF_3CF_2O(CF_2CF_2O)_tCF_2$- | $0 \leq t \leq 6$ |
| and $CF_3(CF_2)_2O[CF(CF_3)CF_2O]_uCF(CF_3)$- | $0 \leq u \leq 6$ | and W is selected from the group consisting of:
—$(CH_2)_n$—,
—$(CH_2)_p CH=CH-(CH_2)_q$—,
—$(CH_2)_m$—CO—,
—$(CH_2)_j OCH_2CH(OH)CH_2$—, and
—$(CH_2)_k OCH_2CH(CH_2OH)$—,
wherein in the last three cases $R_F$ is bonded to the carbon atom of the left end of the W group; n=1 to 12; m=0 to 12; (p+q)=1 to 12; and j and k individually are from 1 to 12;
it being understood that W can still contain a —$(CH_2CH_2O)_y$— polyoxyethylene, a —$(CH(CH_3)CH_2O)_y$-polyoxypropylene or a —$(CH_2CH_2S)_y$-polythioethylene segment, or a mixture of such segments, with $1 \leq y \leq 12$, and that in the $R_F$— chain, part of the fluorine atoms can be replaced by H, Cl or Br atoms, in a proportion such that at least 50% of the atoms bonded to the carbon skeleton of $R_F$— are fluorine atoms, with at least 4 fluorine atoms being present in said chain, so as to obtain:
in cases (a) and (d) respectively an ether or ester of the type $R_F$—W—O—(hydrophilic moiety),
and in cases (b) and (c) respectively an amine or amide of the type $R_F$—W—N(R'')-(hydrophilic moiety),
and by the fact that the protected groups, when present, are subjected to a deprotection reaction.

8. A process according to claim 6 or 7, for preparing a compound of formula I, X—Y—CH(OR$_1$)—CH(OR$_2$)—CH(OR$_3$)—Z; wherein
X represents —CH=O, —CH$_2$OR$_4$, —CH$_2$N(R$_5$)R$_6$ or —CH(OR$_7$)—,
Y represents —CH(OR$_8$)—, —CO— or —CH(NR$_5$R$_6$)—,
Z represents —H, —CH$_3$, —CH$_2$OR$_9$ or —CH(OR$_{10}$)—,
it being understood that:
when X is —CH=O, then Y represents —CH(OR$_8$)— or —CH(NR$_5$R$_6$)—,
when X is —CH$_2$N(R$_5$)R$_6$, then Y represents —CH(OR$_8$)—,
when Z is —CH(OR$_{10}$)—, then X represents —CH(OR$_7$)— and then the divalent groups X and Z are linked together through a covalent bond; and
when Y is —CH(NR$_5$R$_6$)—, the X represents —CH=O or —CH$_2$OR$_4$, and the R$_1$ to R$_{10}$ groups, which may be identical or different, are selected from —H, C$_1$-C$_{18}$ alkyl, C$_2$-C$_{18}$ unsaturated alkyl, a deoxyoside group, a —(CH$_2$CH$_2$O)$_y$—H, —[CH(CH$_3$)CH$_2$O]$_y$ —H or (CH$_2$CH$_2$S)$_y$—H group, or a mixture of said groups, wherein $1 \leq y \leq 12$, and a highly fluorinated group as defined above;
with the proviso that at least one of the R$_1$ through R$_{10}$ groups represents a group having a highly fluorinated substituent; and internal ethers and ketals thereof, wherein:
either the starting material is a compound similar to a compound of formula I, but having no highly fluorinated group, and R$_5$ and R$_6$, when present, are different from —H, and wherein the —OH groups of said starting material which are not desired to be substituted are temporarily protected, said starting material is reacted with an acyl chloride R$_F$—W—Cl (when R$_F$—W— is an acyl) or with a compound R$_F$—W—Z' (when R$_F$—W— is different from an acyl), where Z' is —OH or a leaving group, so as to obtain respectively the corresponding ester or ether of formula I, and then the protected groups are subjected to a deprotection reaction;

or the starting material is a compound similar to a compound of formula I, but having no highly fluorinated group, wherein at least one of the —OR$_1$, —OR$_2$, —OR$_3$, —OR$_4$, —OR$_7$, —OR$_9$, OR$_{10}$ or —NR$_5$R$_6$ groups is replaced by a leaving group, and wherein the —OH groups are protected, said starting material is reacted with an alcohol R$_F$—W—OH or amine R$_F$—W—NHR", wherein R$_F$—W— is other than acyl and R" is —H, C$_1$-C$_{18}$ alkyl, C$_2$-C$_{18}$ unsaturated alkyl, or R$_F$—W—, so as to obtain a corresponding compound of formula I wherein the leaving group of the starting material is replaced respectively by a —O—W—R$_F$ or —N(R")—W—R$_F$ substituent, and then the protected groups are subjected to a deprotection reaction;

or the starting material is a compound similar to a compound of formula I, having a —NR$_5$R$_6$ group, but having no highly fluorinated group, wherein at least one of R$_5$ and R$_6$ is —H, said starting material is reacted with a mixed anhydride of the formula R$_F$—W—O—CO—OAlk (R$_F$—W— being an acyl and Alk being lower alkyl), so as to obtain a corresponding amide of formula I having a —NR$_5$(R$_F$W), —NR$_6$(R$_F$W) or —N(R$_F$W)$_2$ group; and wherein R$_F$—W represents a group wherein R$_F$ is selected from the group consisting of:

| | |
|---|---|
| F(CF$_2$)$_v$- | with 2 ≦ v ≦ 12 |
| (CF$_3$)$_2$CF(CF$_2$)$_w$- | 0 ≦ w ≦ 8 |
| R$_F$1[CF$_2$CF(CF$_3$)]$_r$- | 1 ≦ r ≦ 4 |

R$_F$1 being CF$_3$—, C$_2$F$_5$— or (CF$_3$)$_2$CF—,

| | | |
|---|---|---|
| R$_F$2<br>R$_F$3 | CFO(CF$_2$CF$_2$)$_s$- | 1 ≦ s ≦ 6 |

R$_F$2 and R$_F$3, identical or different, being selected from CF$_3$—, C$_2$F$_5$—, n-C$_3$F$_7$ or CF$_3$CF$_2$CF(CF$_3$)—, or R$_F$2 and R$_F$3 representing together —(CF$_2$)$_4$— or —(CF$_2$)$_5$—,

| | |
|---|---|
| CF$_3$CF$_2$O(CF$_2$CF$_2$O)$_t$CF$_2$- | 0 ≦ t ≦ 6 |
| and CF$_3$(CF$_2$)$_2$O[CF(CF$_3$)CF$_2$O]$_u$CF(CF$_3$)- | 0 ≦ u ≦ 6 | and W is selected from the group consisting of:
—(CH$_2$)$_n$—
—(CH$_2$)$_p$CH=CH—(CH$_2$)$_q$—
—(CH$_2$)$_m$—CO—
—(CH$_2$)$_j$OCH$_2$CH(OH)CH$_2$—, and
—(CH$_2$)$_k$OCH$_2$CH(CH$_2$OH)—
wherein in the last three cases R$_F$ is bonded to the carbon atom of the left end of the W group; n=1 to 12; m=0 to 12; p+q=1 to 12; and j and k individually are from 1 to 12;

it being understood that W can still contain a —(CH$_2$CH$_2$O)$_y$— polyoxyethylene, a —CH(CH$_3$)CH$_2$O y polyoxypropylene, or a —(CH$_2$CH$_2$S)$_y$— polythioethylene segment, or a mixture of such segments, with 1≦y≦12, and that in the R$_F$— chain, part of the fluorine atoms can be replaced by H, Cl or Br atoms, in a proportion such that at least 50% of the atoms bonded to the carbon skeleton of R$_F$— are fluorine atoms, with at least 4 fluorine atoms being present in said chain.

9. Compositions in the form of solutions, dispersions, gels, emulsions, or microemulsions in water or any other polar solvent containing non polar compounds or substances, hydrocarbonated or not, and at least one hydrophilic and fluorinated compound as defined in claim 1.

10. A composition according to claim 9, wherein non polar compounds or substances are highly fluorinated or perfluorinated.

11. A composition according to claim 10 wherein said highly fluorinated or perfluorinated compounds or substances, having molecular masses between about 400 and 700, are selected from the group consisting of the bis (F-alkyl)-1,2-ethenes, the perfluorodecalins, the perfluoro-methyldecalins, the perfluoro-dimethyldecalins, the perfluorodimethyladamantanes, the perfluorotrimethylbicyclo-/3,3,1/nonanes and their homologues, ethers of formula (CF$_3$)CFO(CF$_2$CF$_2$) OCF(CF$_3$)$_2$, (CF$_3$)$_2$CFO(CF$_2$CF$_2$)$_3$OCF(CF$_3$)$_2$, (CF$_3$)$_2$CFO(CF$_2$CF$_2$)$_2$F, (CF$_3$)$_2$CFO(CF$_2$CF$_2$)$_3$F, F[CF (CF$_3$)CF$_2$O]$_2$ CHFCF$_3$, (C$_6$F$_{13}$)$_2$O, the amines N(C$_3$F$_7$)$_3$, N(C$_4$F$_9$)$_3$, the perfluoromethylquinolidines and perfluoroisoquinolidines, the halogen derivatives C$_6$F$_{13}$Br, C$_8$F$_{17}$Br, C$_6$F$_{13}$ CBr$_2$CH$_2$Br, 1-bromoheptadecafluoro-4-isopropylcyclohexane and analogues.

12. A composition according to claim 11, wherein said highly fluorinated or perfluorinated compounds are bis(F-butyl)-1,2-ethenes, F-isopropyl-1-F-hexyl-2-ethenes or bis(F-hexyl)-1,2-ethenes.

13. A compound according to claim 1 wherein said hydrophilic moiety is a sugar selected from the group consisting of aldopentoses, ketopentoses, aldohexoses, ketohexoses, 6-deoxyaldohexoses, and 6-deoxyketohexoses.

14. A compound according to claim 1 wherein said hydrophilic moiety is a polyol selected from the group consisting of pentitols, 1-deoxyhexitols, hexitols, and cyclitols.

15. A compound according to claim 1 wherein said hydrophilic moiety is an aminopolyol selected from the group consisting of 1-amino-1-deoxypentitols, osamines, 2-amino-2-deoxypentitols, 1-amino-1,6-dideoxyhexitols, and 1-amino-1-deoxyhexitols.

16. A compound according to claim 1 wherein said hydrophilic moiety is a diholoside selected from the group consisting of maltose, lactose, saccharose, and cellobiose.

* * * * *